United States Patent
Almeida et al.

(10) Patent No.: US 10,918,732 B2
(45) Date of Patent: Feb. 16, 2021

(54) GLYCOCONJUGATES AND METHODS FOR THEIR USE

(71) Applicants: Igor C. Almeida, El Paso, TX (US); Katja Michael, El Paso, TX (US); Nathaniel Schocker, El Paso, TX (US); Susana Portillo, El Paso, TX (US); Rosa Maldonado, El Paso, TX (US)

(72) Inventors: Igor C. Almeida, El Paso, TX (US); Katja Michael, El Paso, TX (US); Nathaniel Schocker, El Paso, TX (US); Susana Portillo, El Paso, TX (US); Rosa Maldonado, El Paso, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 16/523,688

(22) Filed: Jul. 26, 2019

(65) Prior Publication Data
US 2019/0343960 A1 Nov. 14, 2019

Related U.S. Application Data

(63) Continuation of application No. 15/522,631, filed as application No. PCT/US2015/058528 on Oct. 31, 2015, now Pat. No. 10,363,319.

(60) Provisional application No. 62/185,715, filed on Jun. 28, 2015, provisional application No. 62/073,829, filed on Oct. 31, 2014.

(51) Int. Cl.
*A61K 47/64* (2017.01)
*G01N 33/569* (2006.01)

(52) U.S. Cl.
CPC .......... *A61K 47/643* (2017.08); *A61K 47/646* (2017.08); *G01N 33/56905* (2013.01); *G01N 2400/02* (2013.01); *Y02A 50/30* (2018.01)

(58) Field of Classification Search
None
See application file for complete search history.

(56) References Cited

U.S. PATENT DOCUMENTS

RE39,245 E * 8/2006 Nilsson .......................... 435/100

FOREIGN PATENT DOCUMENTS

WO   WO 2014/067970   5/2014

OTHER PUBLICATIONS

Almeida et al., "A highly sensitive and specific chemiluminescent enzyme-linked immunosorbent assay for diagnosis of active Trypanosoma cruzi infection" *Transfusion* 1997, 37:850-857.

Almeida et al., "Complement-mediated lysis of Trypanosoma cruzi trypomastigotes by uman anti-alpha-galactosyl antibodies." *Journal of immunology* 1991, 146:2394-2400.
Almeida et al., "Glycoconjugates of Trypanosoma cruzi: a 74 kD antigen of trypomastigotes specifically reacts with lytic anti-alpha-galactosyl antibodies from patients with chronic Chagas disease" *Journal of clinical laboratory analysis* 1993, 7:307-316.
Almeida et al., *The Biochemical journal* 1994, 304 (Pt 3):793-802.
Ashmus et al., "Potential use of synthetic α-galactosyl-containing glycotopes of the parasite *Trypanosoma cruzi* as diagnostic antigens for Chagas disease" *Organic & biomolecular chemistry* 2013, 11:5579-5583.
Atassi et al., "Immune recognition of serum albumin—XIV. Cross-reactivity by T-lymphocyte proliferation of subdomains3, 6 and 9 of bovine serum albumin" *Mol Immunol* 1982, 19:313-321.
Avila et al., "Immunogenic Gal alpha 1-3Gal carbohydrate epitopes are present on pathogenic American Trypanosoma and Leishmania" *Journal of immunology* 1989, 142:2828-2834.
Benatuil, et al., Eur J Immunol. 35:2638-47, 2005.
Brinkmann et al., 2001. "Chemo-enzymatic synthesis of the Galili epitope Gal(alpha)(1-->3)Galbeta(1-->4) GlcNAc on a homogeneously soluble PEG polymer by a multi-enzyme system." *Bioorganic & Medicinal Chemistry Letters*, 11:2503-2506.
Buscaglia et al., 2004. "The surface coat of the mammal-dwelling infective trypomastigote stage of Trypanosoma cruzi is formed by highly diverse immunogenic mucins," *The Journal of biological chemistry*, 279:15860-15869.
Crich et al., 2001. "Why are the hydroxy groups of partially protected N-acetylglucosamine derivatives such poor glycosyl acceptors, and what can be done about it? A comparative study of the reactivity of N-acetyl-, N-phthalimido-, and 2-azido-2-deoxyglucosamine derivatives in glycosylation. 2-Picolinyl ethers as reactivity-enhancing replacements for benzyl ethers." *Journal of the American Chemical Society*, 123: 6819-6825.
Dahmén et al., 2002. "Synthesis of the Linear B Type 2 Trisaccharide Galα3galβ4glcnacβotmset, and Coupling of the Corresponding 2-Calboxyethyl B-Thioglycoside to Sepharose," *Journal of Carbohydrate Chemistry*, 21(3):189-199.
Danac et al., 2007. "Carbohydrate chain terminators: rational design of novel carbohydrate-based antifungal agents." *ChemBioChem*, 8:1241-1245.
Etlinger et al., 1990. "Use of prior vaccinations for the development of new vaccines." *Science* 249:423-425.
Fang et al., 1998. "Highly Efficient Chemoenzymatic Synthesis of R-Galactosyl Epitopes with a Recombinant α(1 →3)-Galactosyltransferase," *Journal of the American Chemical Society*, 120:6635-6638.
Frasch. "Functional diversity in the trans-sialidase and mucin families in Trypanosoma cruzi." 2000, *Parasitology today*, 16:282-286.
Gavard et al., 2003. "Efficient Preparation of Three Building Blocks for the Synthesis of Heparan Sulfate Fragments: Towards the Combinatorial Synthesis of Oligosaccharides from Hypervariable Regions," *European Journal of Organic Chemistry*, 2003:3603-3620.
Hanessian et al., 2001. "Practical syntheses of B disaccharide and linear B type 2 trisaccharide—non-primate epitope markers recognized by human anti-α-Gal antibodies causing hyperacute rejection of xenotransplants," *Tetrahedron*, 57:3267-3280.

(Continued)

*Primary Examiner* — Brian Gangle
(74) *Attorney, Agent, or Firm* — Norton Rose Fulbright US LLP

(57) ABSTRACT

Certain embodiments are directed to method for synthesizing and using glycoconjugates based on the immunodominant epitope Galα(1,3)Galβ(1,4)GlcNAcα (Galα3LNα).

11 Claims, 10 Drawing Sheets

(56) References Cited

OTHER PUBLICATIONS

Hendel et al., 2009. "How the substituent at O-3 of N-acetylglucosamine impacts glycosylation at O-4: a comparative study." *The Journal of Organic Chemistry*, 74:8321-8331.

Houseman et al., 2003. "Maleimide-Functionalized Self-Assembled Monolayers for the Preparation of Peptide and Carbohydrate Biochips," *Langmuir*, 19:1522-1531.

Hussain, et al., Egyptian J Med Hum Genet. 13:1-9, 2012.

Imamura et al., 2006. "Extended applications of di-tert-butylsilylene-directed alpha-predominant galactosylation compatible with C2-participating groups toward the assembly of various glycosides." *Chemistry—A European Journal*, 12:8862-8870.

International Preliminary Report on Patentability in International Application No. PCT/US2015/058528 dated May 11, 2017.

International Search Report and Written Opinion in International Application No. PCT/US2015/058528 dated Mar. 7, 2016.

Izquierdo et al., 2013. "Evaluation of a chemiluminescent enzyme-linked immunosorbent assay for the diagnosis of Trypanosoma cruzi infection in a nonendemic setting," *Memórias do Instituto Oswaldo Cruz*, 108:928-931.

Khamsi et al., 2012. *Carbohydrate Research*, 357:147-150.

Kiso et al., 1979. "The ferric chloride-catalyzed glycosylation of alcohols by 2-acylamido-2-deoxy-β-D-glucopyranose 1-acetates," *Carbohydrate Research*, 72:C12-C14.

Litjens et al., 2005. "Synthesis of an α-Gal epitope α-D-Galp-(1→3)-β-D-Galp-(1→4)-β-D-Glcp NAc-lipid conjugate," *Journal of Carbohydrate Chemistry*, 24:755-769.

Milland et al., "Carbohydrate residues downstream of the terminal Galα(1,3)Gal epitope modulate the specificity of xenoreactive antibodies" *Immunol. Cell Biol.* 2007, 85: 623-632.

Neethling et al., "The reducing end of αGal oligosaccharides contributes to their efficiency in blocking natural antibodies of human and baboon sera" *Transplant International* 1996, 9:98-101.

Plaza-Alexander et al., 2013. "Synthesis of trisaccharides incorporating the α-Gal antigen functionalized for neoglycoconjugate preparation," *Arkivoc*, ii:112-122.

Qian et al., 1999. "Chemoenzymatic Synthesis of α-(1→3)-Gal(NAc)-Terminating Glycosides of Complex Tertiary Sugar Alcohols," *Journal of the American Chemical Society*, 121:12063-12072.

Schmidt et al., 1980. "Facile Synthesis of α- and β-O-Glycosyl Imidates; Preparation of Glycosides and Disaccharides," *Angew Chem Int Edit*, 19:731-732.

Sherman et al., 2001. "Study of glycosylation with N-trichloroacetyl-D-glucosamine derivatives in the syntheses of the spacer-armed pentasaccharides sialyl lacto-N-neotetraose and sialyl lacto-N-tetraose, their fragments, and analogues." *Carbohydrate Research*, 336:13-46.

Soares et al., 2012. *The American journal of tropical medicine and hygiene*, 87:87-96.

Stevenson et al., 1996. "Synthesis of allyl beta-D-galactopyranoside from lactose using *Streptococcus thermophilus* beta-D-galactosidase." *Carbohydrate Research*, 284:279-283.

Tearle et al., 1996. "The alpha-1,3-galactosyltransferase knockout mouse. Implications for xenotransplantation." *Transplantation*, 61:13-19.

Travassos et al., 1993. "Carbohydrate immunity in American trypanosomiasis." *Springer Semin Immunopathol*, 15:183-204.

Wilkinson, 1996. "Bacterial lipopolysaccharides—themes and variations." *Progress in lipid research*, 35:283-343.

Yoshida et al., 2001. "Synthesis of a set of di- and tri-sulfated galabioses." *Carbohydrate Research*, 335:167-180.

\* cited by examiner

A

B

GLYCOCONJUGATES AND METHODS FOR THEIR USE

CROSS-REFERENCE TO RELATED APPLICATIONS

The present application is a continuation from U.S. application Ser. No. 15/522,631 filed Apr. 27, 2017 which is a national-phase application under 35 U.S.C. § 371 from PCT/US2015/058528 filed Oct. 31, 2015, which claims priority to U.S. Provisional Application Nos. 62/073,829 filed Oct. 31, 2014 and 62/185,715 filed on Jun. 28, 2015, each of which is incorporated herein by reference in its entirety.

STATEMENT REGARDING FEDERALLY FUNDED RESEARCH

This invention was made with government support under Grant Nos. RR08124 and GM008012 awarded by the National Institutes of Health. The government has certain rights in the invention.

BACKGROUND

Chagas disease (ChD) is a tropical disease resulting from parasite infection with an estimated 8 to 14 million chronic cases in Latin America, and has also become a public health concern in the U.S., Europe, and other nonendemic regions. Current treatment for ChD is limited to two drugs, benznidazole and nifurtimox, which have limited efficacy and serious side effects. There is no preventive or therapeutic vaccine for human ChD. Over the years, various groups have developed experimental vaccines, using mainly parasite lysates, purified or recombinant proteins and peptides, and DNA, targeting almost exclusively protein antigens. Most, if not all, of these vaccines have failed to provide protection to animals challenged with different parasite strains.

Patients with acute or chronic Chagas disease (ChD), from diverse geographical locations in Latin America, have very high titers of trypanolytic, protective anti-α-galactosyl antibodies (Ch anti-α-Gal Abs). These antibodies are protective and thought to be the major host immune mechanism controlling parasitemia at both acute and chronic stages of ChD. Ch anti-α-Gal Abs recognize highly immunogenic terminal, non-reducing α-Gal-containing epitopes abundantly expressed on major immunodominant glycoproteins (such as mucins and TS/gp85 glycoproteins) of the mammal-dwelling trypomastigote form. Since these α-Gal epitopes are absent in human cells, it is contemplated that an effective human ChD vaccine is obtained using these immunodominant B-cell epitopes. An α-Gal-based vaccine, however, has thus far been hindered by (a) technical difficulties related to purification, structural analysis, and synthesis of α-Gal-containing glycans; and (b) lack of a suitable animal model that closely mimics the specific human anti-α-Gal response.

There remains a need for therapeutic and preventative compositions for the treatment and characterization of parasitic disease such as Chagas disease.

SUMMARY

The protozoan parasite, *Trypanosoma cruzi*, the etiologic agent of Chagas disease, has a cell surface covered by immunogenic glycoconjugates. One of the immunodominant glycotopes, the trisaccharide Galα(1,3)Galβ(1,4)GlcNAcα, is expressed on glycosylphosphatidylinositol-anchored mucins of the infective trypomastigote stage of *T. cruzi* and triggers high levels of protective anti-α-Gal antibodies in infected individuals. Embodiments described herein are directed to efficiently synthesizing the mercaptopropyl glycoside of that glycotope and conjugating the glycotope to a maleimide-derivatized carrier.

Certain embodiments are directed to a neoglycoconjugate comprising a trisaccharide coupled to a carrier. In certain aspects the neoglycoconjugate includes a linker or spacer connecting the trisaccharide to the carrier. The carrier can be a protein carrier, peptide carrier, or nanoparticle carrier. In certain aspects the protein carrier is bovine serum albumin. In other aspects the peptide carrier is a T cell epitope. The trisaccharide of the neoglycoconjugate can include a terminal (1,3)α-galactose residue. In certain aspects the trisaccharide is Galα(1,3)Galβ(1,4)GlcNAcα. In a particular aspect the neoglycoconjugate is a conjugate of Galα(1,3)Galβ(1,4)GlcNAcα to bovine serum albumin.

A further embodiment is directed to methods for chemical synthesis of a mercaptopropyl glycoside. In certain aspects the methods include (a) converting an acyl-protected allyl disaccharide to a trichloroacetimide donor; (b) glycosylating the trichloroacetimide donor with a allyl-glycoside donor forming a trisaccharide allyl-glycoside; (c) derivatizing the trisaccharide allyl-glycoside to a mercaptopropyl glycoside; and (d) conjugating the mercaptopropyl glycoside to a carrier forming a neoglycoconjugate. The disaccharide can be Galα(1,3)Galβ(1,4). The allyl-glycoside donor can be an allyl-GlcNAcα. The carrier can be a protein carrier or peptide carrier. In certain aspects the protein carrier is bovine serum albumin. In a particular aspect the mercaptopropyl glycoside is a glycoside of Galα(1,3)Galβ(1,4)GlcNAcα.

In certain aspects an acyl-protected allyl disaccharide is produced by (i) p-methoxybenzylation of allyl glycoside at position 3 via its tin acetal followed by benzoylation of remaining hydroxyls; (ii) oxidatively cleaving the p-methoxybenzoyl group with 2,3-dichloro-5,6-dicyano-1,4-benzoquinone to produce an allyl glycoside acceptor; (iii) glycosylating a di-tert-butylsilylidene equipped α-Gal trichloroacetimidate donor with the allyl glycoside acceptor using a trimethylsilyl trifluoromethanesulfonate catalysis to give di-tert-butylsilylidene disaccharide; (iv) cleaving the di-tert-butylsilylidene by exposing the disaccharide to hydrogen fluoride in pyridine; and (v) acetylation of the hydroxyls to form the acyl-protected allyl disaccharide.

In a further aspect the method of glycosylating the trichloroacetimide donor includes (i) treating the trichloroacetimide donor with palladium (II) chloride in methanol to produce a hemiacetal; (ii) reacting the trichloroacetimide hemiacetal with trichloroacetonitrile in the presence of 1,8-diazabicycloundec-7-ene converting the trichloroacetimide hemiacetal into a trichloroacetimidate; (iii) reacting the trichloroacetimidate with allyl 2-deoxy-2-azido-Glc acceptor and reducing product with neat thioacetic acid to give an N-acetyl trisaccharide; (iv) reacting the N-acetyl trisaccharide with thioacetic acid and azobisisobutyronitrile in tetrahydrofuran under UV light to produce a thioester trisaccharide; and (v) saponifying the thioester trisaccharide under Zemplen conditions to produce a mercaptopropyl trisaccharide.

Other embodiments are directed to a non-natural glycoprotein (neoglycoprotein) comprising a protein carrier conjugated to a glycan, wherein the glycan comprises a terminal, non-reducing αGal residue. In certain aspects the glycan can be a trisaccharide. In a particular aspect the trisaccharide is a Galα(1,3)Galβ(1,4)GlcNAcα. The protein carrier can be albumin, and in particular bovine serum albumin (BSA). The glycoprotein can include a linker connecting the glycan to the protein carrier. In certain aspects the non-natural glycopeptide (neoglycopeptide) comprising a peptide carrier conjugated to a glycan, wherein the glycan comprises a terminal, non-reducing αGal residue.

Certain embodiments are directed to a non-natural glycoconjugate (neoglycoconjugate) comprising a peptide carrier conjugated to a glycan, wherein the glycan comprises a terminal, non-reducing αGal residue. In certain aspects the glycan can be a trisaccharide. In a particular aspect the trisaccharide is a Galα(1,3)Galβ(1,4)GlcNAcα. The peptide carrier can be T cell epitope. The glycoconjugate can include a linker connecting the glycan to the peptide carrier. In certain aspects the non-natural glycoconjugates includes a peptide carrier conjugated to a glycan, wherein the glycan comprises a terminal, non-reducing αGal residue.

Still further embodiments are directed to methods for detecting a parasite that include (a) contacting a blood sample from a subject with a neoglycoprotein or a neoglycopeptide, wherein the neoglycoprotein or a neoglycopeptide forms a complex with antibodies in the blood sample that bind a glycan having a terminal αGal; and (b) detecting the formation of an antibody-neoglycoprotein or neoglycopeptide complex, wherein detection of antibody binding above background indicates a parasite infection. The subject can be suspected of having Chagas disease, leishmaniasis, or malaria.

Other embodiments are directed to methods of inducing an immune response to a parasite comprising administering a neoglycoconjugate, neoglycoprotein, or a neoglycopeptide to a subject, wherein the subject develops an immune response to glycans having a terminal αGal moiety.

Certain embodiments are directed to methods for inducing an immune response against *T. cruzi* in a human comprising administering a Galα(1,3)Galβ(1,4)GlcNAcα antigen, wherein an immune response is generated against a *T. cruzi*. In certain aspects the Galα(1,3)Galβ(1,4)GlcNAcα antigen coupled to a carrier. In a particular aspect the carrier is bovine serum albumin.

The synthetic Galα(1,3)Galβ(1,4)GlcNAcα (Galα3LNα or Galα3LN) and other linear or branched αGal-containing glycotopes (where the linear glycotope or at least one or more of the branched glycotopes includes, but it is not restricted to Galα(1,3)Galβ(1,4)GlcNAcα, Galα(1,3)Galβ(1,4)GlcNAcβ, Galα(1,3)Galβ(1,4)Glcα, Galα(1,3)Galβ(1,4)Glcβ, Galα(1,3)Galβ, Galα(1,3)Galα, Galα(1,2)Galβ(1,4)GlcNAcα, Galα(1,2)Galβ(1,4)GlcNAcβ, Galα(1,2)Galβ(1,4)Glcα, Galα(1,2)Galβ(1,4)Glcβ, Galα(1,2)Galβ, Galα(1,2)Galα and other embodiments thereof) coupled to a carrier protein or peptide (neoglycoconjugate) can be used as diagnostic or prognostic (chemotherapy follow-up) biomarkers, or vaccines for parasitic diseases, such as Chagas disease. These neoglycoconjugates can be employed for treating or detecting other protozoan and helminth parasites, such as those involved in visceral, cutaneous, and mucocutaneous leishmaniasis; malaria; African trypanosomiasis; and hookworm (necator or ancylostoma), and tapeworm (cestodes) infections.

Glycoconjugates (glycolipids and glycoproteins) are major antigens on surface of *T. cruzi* and contain highly immunogenic epitopes. The antigens remain largely unexplored as vaccine targets. Certain embodiments described herein are directed to glycoconjugate antigens from or mimicking *Trypanosoma cruzi* glycoconjugate(s). The immunogenic epitopes contained in the glycoconjugate antigens of *T. cruzi* are reproduced and used as an immunogen. A mouse model has been used that mimics a human response to *T. cruzi* infection or exposure in the U.S. (U. Michigan) (Tearle et al., 1996) and Australia (St Vincent's Hospital, Melbourne) (Thall et al., 1996)). In certain aspects, the reproduced glycoconjugate antigens and immunogenic epitopes thereof can be administered as a vaccine. In certain aspects the vaccine is validated in a mouse model, as described herein. In still further aspects, a glycoconjugate-based vaccine can be used to induce a long-lasting, full-protection against *T. cruzi*.

Certain embodiments are directed to inducing an immune response by administering Galα(1,3)Galβ(1,4)GlcNAcα (Galα3LNα) to a subject. In certain aspects the subject is human. In certain aspects the Galα3LNα is synthetic. In certain aspects, the epitope comprises a Galα1,3Galβ epitope. In certain aspects 1, 2, 3, 4, 5, 6, or more Galα1,3Galβ epitopes are coupled to a protein or peptide support (neoglycoprotein or neoglycopeptide) or adjuvant. The Galα1,3Galβ epitope is strongly recognized by parasite-induced anti-α-Gal Abs and to a much less extent by natural anti-α-Gal Abs from healthy individuals (NHS anti-α-Gal Abs). The Galα3LNα epitope is capable of inducing lytic, protective antibodies (i.e., Chagasic anti-α-Gal Abs) produced during both the acute and chronic stages of Chagas disease. In certain embodiments, synthetic Galα3LN and neoglycopeptides are used as preventative compositions. In certain embodiments, synthetic Galα3LNα and neoglycopeptides are used as a therapeutic.

Galα1, 3Galβ1, 4GlcNAcα–R
R = aglycon (a linker through which the glycan is linked to a protein or peptide)

Certain embodiments are directed to a glycoconjugate-based vaccine that induces a long-lasting, full protection against *T. cruzi*. In certain aspects the glycoconjugate-based vaccine's protection is mediated by B cells. In a further aspect the glycoconjugate-based vaccine's protection is dependent on CD4+ T cells and/or CD8+ T cells.

In certain aspects, the glycoconjugate-based vaccine candidates are structurally simple and synthetic. In certain aspects the glycoconjugate-based vaccine candidates can be produced in large scale. In still further aspects, the glycoconjugate-based vaccine candidates are chemically stable.

Certain embodiments are directed to a method of screening antigens by mimicking the human B cell-mediated immune response to *T. cruzi*. In certain aspects, the method of screening antigens by mimicking the human B cell-mediated immune response to *T. cruzi* is carried out using a mouse model—the mouse model being a α-1,3-galactotransferase-knockout mouse. The α-1,3-galactotransferase-knockout mice do not express Galα1,3Gal epitopes on their cells due to the disruption of the enzyme α-1,3-galactosyltransferase.

As used herein, the term "subject" or "patient" refers to any mammal, including humans. In certain aspects the methods of the present invention are applied to human subjects or human patients.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or 'containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DESCRIPTION

Figure 1:
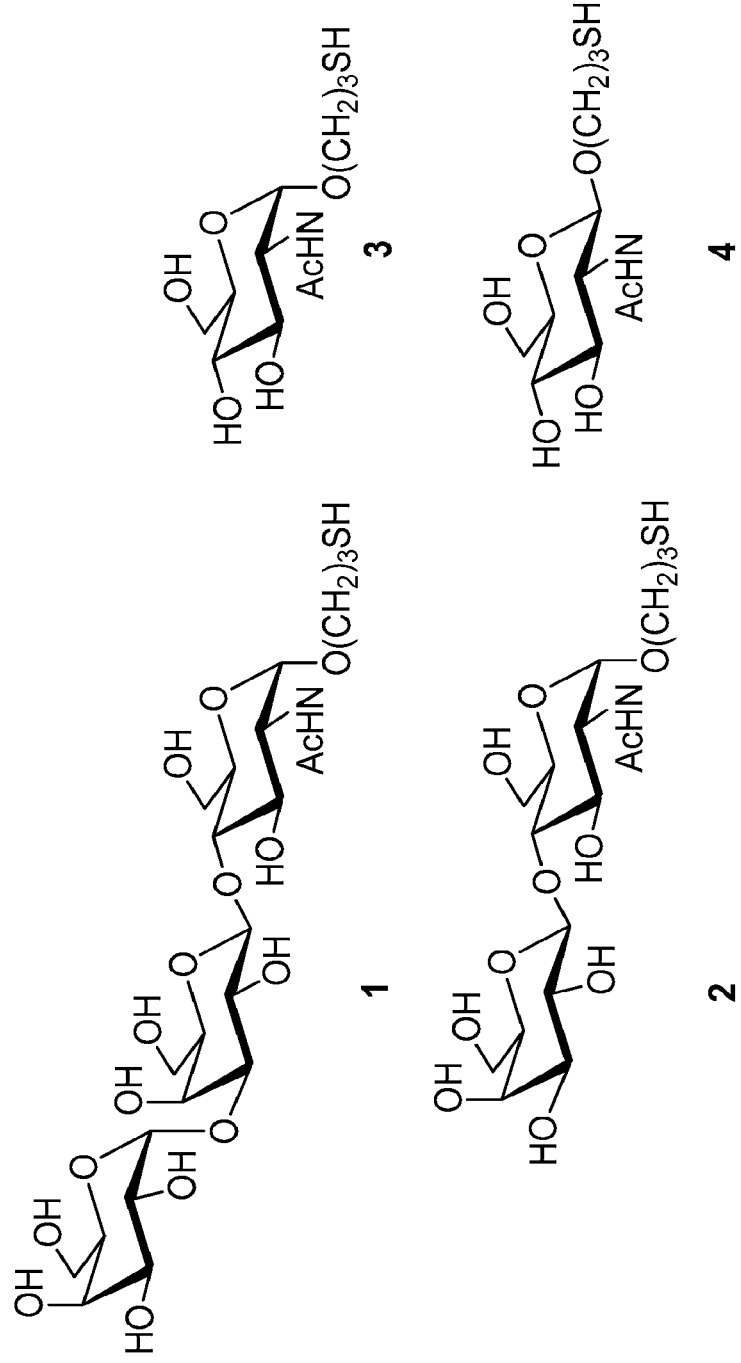
FIG. 1. Target mercaptopropyl saccharides of Galα(1,3)Galβ(1,4)GlcNAcα (1), Galβ(1,4)GlcNAcα (2), GlcNAcα (3), and GlcNAcβ (4).

The protozoan parasite, *Trypanosoma cruzi*, the etiologic agent of Chagas disease, has a cell surface covered by immunogenic glycoconjugates. One of the immunodominant glycotopes, the trisaccharide Galα(1,3)Galβ(1,4)GlcNAcα, is expressed on glycosylphosphatidylinositol-anchored mucins of the infective trypomastigote stage of *T. cruzi* and triggers high levels of protective anti-α-Gal antibodies in infected individuals. Embodiments described herein are directed to efficiently synthesizing the mercaptopropyl glycoside of a glycotope and conjugating the glycotope to a maleimide-derivatized carrier protein, such as but not limited to bovine serum albumin (BSA). Chemiluminescent-ELISA revealed that Galα(1,3)Galβ(1,4)GlcNAcα-BSA is recognized by purified anti-α-Gal antibodies from chronic Chagas disease patients 230-fold more strongly than by anti-α-Gal antibodies from sera of healthy individuals (NHS anti-αGal). Similarly, the pooled sera of chronic Chagas disease patients (ChHSP) recognized Galα(1,3)Galβ(1,4)GlcNAcα approximately 20-fold more strongly than pooled normal healthy serum (NHS). In contrast, the underlying disaccharide Galβ(1,4)GlcNAcα, and the monosaccharide GlcNAcα or GlcNAcβ conjugated to BSA are poorly or not recognized by purified anti-α-Gal antibodies or sera from Chagasic patients or healthy individuals. These results highlight the importance of the terminal Galα moiety for recognition by Ch anti-α-Gal antibodies and the lack of antibodies against non-self Galβ(1,4)GlcNAcα and GlcNAcα glycotopes.

The substantial difference in binding of Ch vs. NHS anti-α-Gal antibodies to Galα(1,3)Galβ(1,4)GlcNAcα-BSA suggests that this neoglycoprotein is suitable for vaccine development. To this end, the Galα(1,3)Galβ(1,4)GlcNAcα-BSA neoglycoprotein was used to immunize α1,3-galactosyltransferase-knockout (α1,3GalT-KO) mice, which produced antibody titers 40-fold higher as compared to pre-immunization titers. The synthetic Galα(1,3)Galβ(1,4)GlcNAcα and other linear or branched αGal-containing glycotopes (and embodiments thereof) coupled to a carrier protein or peptide could be used as diagnostic or prognostic (i.e., chemotherapy follow-up) biomarkers, or vaccine candidates for parasitic diseases, such as Chagas disease. These neoglycoconjugates can be employed for applications in visceral, cutaneous and mucocutaneous leishmaniasis; malaria; African trypanosomiasis; and hookworm and tapeworm infections.

Glycoconjugates (glycolipids and glycoproteins) are major antigens on the surface of *T. cruzi* and contain highly immunogenic epitopes. The antigens remain largely unexplored as vaccine targets. Certain embodiments described herein are directed to glycoconjugate antigens from or mimicking *T. cruzi* glycoconjugate(s). The immunogenic epitopes contained in the glycoconjugate antigens of *T. cruzi* are reproduced and used as an immunogen. As described herein a mouse model that mimics a human response to *T. cruzi* infection or exposure was used to characterize the glycoconjugates described herein. In certain aspects, the glycoconjugate antigens and immunogenic epitopes can be administered as a vaccine. In certain aspects the vaccine is validated in a mouse model, as described herein. In still further aspects, a glycoconjugate-based vaccine can be used to induce a long-lasting, full-protection against *T. cruzi*.

The immunodominant glycotope (glycan epitope), Galα(1,3)Galβ(1,4)GlcNAcα, is abundantly expressed in the mammal-dwelling *T. cruzi* trypomastigote stage (Almeida et al. 1994) and is not expressed on human cells, thus it is highly immunogenic to humans (Macher and Galili 2008, Travassos and Almeida 1993). The Galα(1,3)Galβ(1,4)GlcNAcα epitope contains a terminal, non-reducing αGal residue, which is highly conserved on trypomastigote-derived GPI-mucins (tGPI-mucins) of at least four major *T. cruzi* genotypes causing ChD in humans: TcI, TcII, TcV, and TcVI (Almeida et al. 1993, Izquierdo et al. 2013, Soares et al. 2012, Travassos and Almeida 1993).

The Galα(1,3)Galβ(1,4)GlcNAcα glycotope contains the disaccharide Galα1,3Galβ, which is strongly recognized by Chagasic (Ch) anti-α-Gal Abs and to a much lesser extent by the natural anti-α-Gal Abs from healthy individuals (NHS anti-α-Gal) (Almeida et al. 1994, Ashmus et al. 2013), which are produced mainly against Gram-negative enterobacteria of the human flora (Galili et al. 1999). These enterobacteria (e.g., *E. coli*, *Enterobacter* spp., *Serratia* spp., *Salmonella* spp., *Shigella* spp., *Klebsiella* spp., and *Citrobacter* spp.) have various types of non-reducing, terminal α-Gal-linked glycans, mostly Galα1,2-R, Galα1,4-R, and Galα1,6-R (where R is the remaining side chain or core glycan) on the lipopolysaccharide (LPS) core oligosaccharides or O-antigens (Wilkinson 1996). The glycotope Galα(1,3)Galβ(1,4)GlcNAcα, so far not reported in enterobacteria, and most likely other as-yet unidentified *T. cruzi*-specific cell surface saccharides with terminal αGal moieties, induce the major lytic, protective antibodies (Ch anti-α-Gal Abs) produced during both the acute and chronic stages of ChD (Almeida et al. 1994; Almeida et al. 1991; Avila et al. 1989; Gazzinelli et al. 1991; Milani and Travassos 1988; Travassos and Almeida 1993). These studies strongly indicate that lytic Ch anti-α-Gal Abs could be one of the main immunological mechanisms for controlling the parasitemia in both stages of the disease in humans. Thus, Galα(1,3)Galβ(1,4)GlcNAcα offers a potential route toward a carbohydrate-based vaccine against Chagas disease. Glycoconjugates are still unexplored as vaccine targets in *T. cruzi*, although these molecules are the most abundant and immunogenic antigens on the plasma membrane of all *T. cruzi* developmental stages (Acosta-Serrano et al. 2007; Buscaglia et al. 2004; Frasch 2000).

Embodiments described herein are directed to synthesizing glycosides of Galα(1,3)Galβ(1,4)GlcNAcα, and its truncated versions Galβ(1,4)GlcNAcα and GlcNAcα, as well as its diastereomer GlcNAcβ, all equipped with a thiol functionality (glycosides 1-4, FIG. 1) for their conjugation to the carrier protein bovine serum albumin (BSA). All neoglycoproteins (NGPs) were immunologically evaluated by chemiluminescent enzyme-linked immunosorbent assay (CL-ELISA) (Almeida et al., 1997), using purified Ch anti-α-Gal Abs vs. NHS anti-α-Gal Abs, and Ch human serum pool (ChHSP) vs. normal human serum pool (NHSP). Lastly, the NGP Galα(1,3)Galβ(1,4)GlcNAcα-BSA was used to immunize α1,3-galactosyltransferase-knockout (α1,3GalT-KO) mice, which do not express terminal αGal epitopes in their cells (Tearle et al. 1996; Thall et al. 1996). These animals are able to produce lytic anti-α-Gal Abs, mimicking therefore the human humoral immune response against *T. cruzi* (Almeida et al., unpublished data).

I. GLYCOSIDE AND CONJUGATE SYNTHESIS

The production of the trisaccharide Galα(1,3)Galβ(1,4) GlcNAcα and related analogs has been previously accomplished for a variety of uses, and mostly involves chemoenzymatic syntheses (Brinkmann et al. 2001; Fang et al. 1998; Qian et al. 1999; Vic et al. 1997), which are often efficient. However, some research groups prefer its chemical synthesis due to reagent availability, scalability, and derivatization options. For example, α-Gal trisaccharides have been chemically synthesized and coupled to Sepharose (Dahmén et al. 2002), attached to a lipid for non-covalent association to target molecules (Litjens et al. 2005), or attached to linkers such as p-nitrophenol esters (Plaza-Alexander and Lowary 2013) and 3-aminopropyl groups (Hanessian et al. 2001; Wang et al. 2005) to allow for further functionalization.

Four features of the methods described herein for synthesis of an Galα(1,3)Galβ(1,4)GlcNAcα-containing NGP are: (i) predominant use of acyl protecting groups that can be easily installed and cleanly removed; (ii) utilization of 4,6-di-tertbutylsilyl protected galactosyl donor (Imamura et al. 2006) to ensure a stereoselective α-galactosylation; (iii) utilization of easily accessible monosaccharide building blocks; and (iv) use of an allyl glycoside at the non-reducing end of the trisaccharide allowing for the installation of a thiol functional group, via a thiol-ene reaction, for covalent conjugation to a carrier protein. Implementing these features, the strategy involves the synthesis of an acyl-protected disaccharide (Galα1,3Galβ), its conversion into a trichloroacetimidate donor, glycosylation of an appropriate allylglycoside GlcNAc acceptor to produce a Galα(1,3)Galβ1, 4)GlcNAcα allyl glycoside, and further derivatization into a mercaptopropyl glycoside needed for protein conjugation.

The neoglycoconjugates comprise a glycan attached to a carrier. The glycan can be attached via linker. In certain aspects the carrier can be a protein, peptide, or particle.

In one example BSA was chosen for the generation of NGPs because of its large number of conjugation sites per BSA molecule, its solubility properties, and its suitability as a carrier protein (Makela and Seppala, 1986) and provider of T cell epitopes for the immunization of mice (Atassi et al., 1982), as well as its capability to attach non-covalently to wells of microtiter plates. Previously, it was discovered that Ch anti-α-Gal Abs recognize the disaccharide Galα(1,3) Galβ, which comprises the two terminal sugars of the glycotope trisaccharide Galα(1,3)Galβ(1,4)GlcNAcα, much more strongly than Galα alone (Ashmus et al., 2013). In order to obtain information on the importance of Galβ(1,4) GlcNAcα or GlcNAc for antibody recognition, three additional BSA NPGs containing Galβ1,4GlcNAcα, GlcNAcα, or GlcNAcβ were synthesized and tested by CL-ELISA.

Other suitable carrier proteins include human serum albumin (HSA), keyhole limpet hemocyanin (KLH), ovalbumin (OVA), tetanus toxoid (TT), recombinant proteins from *T. cruzi* containing CD4 and/or CD8 T cell epitopes, *Neisseria meningitidis* outer membrane protein complex, synthetic peptides, heat shock proteins, pertussis proteins, cytokines, lymphokines, hormones, growth factors, artificial proteins comprising multiple human CD4+ T cell epitopes from various pathogen-derived antigens, protein D from *Haemophilus influenzae*, pneumolysin or its non-toxic derivatives, pneumococcal surface protein PspA, iron-uptake proteins, toxin A or B from *Clostridium difficile*, recombinant Pseudomonas aeruginosa exoprotein A (rEPA) and the like.

In certain aspects the carrier can include one or more T-cell epitope. T cell epitopes, e.g., CD4+ T helper cell epitopes (Etlinger et al., 1990), are peptides that can induce T cell help and are known in the art. Epitopes that are useful in the present methods and compositions include those from diphtheria toxoid (DT), tetanus toxin (TI), *Plasmodium falciparum circumsporozite*, hepatitis B surface antigen, hepatitis B nuclear core protein, *H. influenzae* matrix protein, *H. influenzae* haemagglutinin, group B *N. meningitidis* outer membrane protein complex (OMPC), the pneumococcal toxin pneumolysin, and heat shock proteins, including those recombinantly produced and detoxified variants thereof.

In certain aspects the T cell epitope may not include any lysine residues internally, but will be modified to include at least one lysine residue at an end, e.g., at the C terminus. In some embodiments, there is only one lysine residue at the C terminus or at the N terminus. In some embodiments, there will also be one or more amino acids between the carrier peptide sequence and the glycan component of the neoglycoconjugate, i.e., an amino acid spacer sequence. Such spacer sequences can be any amino acid, and will generally be flexible and have small R groups, to avoid steric hindrance and allow for optimal positioning of the linked carbohydrate for presentation to T cells and access of the peptide epitope to bind to an effector cell. Exemplary amino acids suitable for inclusion in the linker include glycine, alanine, and serine. In certain aspects the spacer does not contain lysine residues. In certain embodiments two or more carrier peptides are linked or cross-linked with two or more other carrier peptides.

In other embodiments the carrier may be a nanoparticle carrier. The glycan or glycotope can be linked to biocompatible nanoparticles, with or without a linker or spacer between the glycan and the nanoparticle. The nanoparticles useful in the methods and compositions described herein are made of materials that are (i) biocompatible, i.e., do not cause a significant adverse reaction in a living animal when used in pharmaceutically relevant amounts; (ii) feature functional groups to which the binding moiety can be covalently attached, (iii) exhibit low non-specific binding of interactive moieties to the nanoparticle, and (iv) are stable in solution, i.e., the nanoparticles do not precipitate. The nanoparticles can be monodisperse (a single crystal of a material, e.g., a metal, per nanoparticle) or polydisperse (a plurality of crystals, e.g., 2, 3, or 4, per nanoparticle).

A number of biocompatible nanoparticles are known in the art, e.g., organic or inorganic nanoparticles. Liposomes, dendrimers, carbon nanomaterials and polymeric micelles are examples of organic nanoparticles. Quantum dots can also be used. Inorganic nanoparticles include metallic nanoparticle, e.g., Au, Ni, Pt and $TiO_2$ nanoparticles. Magnetic nanoparticles can also be used, e.g., spherical nanocrystals of 10-20 nm with a $Fe^{2+}$ and/or $Fe^{3+}$ core surrounded by dextran or PEG molecules. In some embodiments, colloidal gold nanoparticles are used, e.g., as described in U.S. Pat. Nos. 7,060,121; 7,232,474.

The linkers or spacers can polymer or amino acid linkers. The linker or spacer will comprise a functional group that provide for attachment to the glycan and another functional group that provides for attachment to the carrier. A variety of linker molecules may be used, using conventional procedures. The linker can be any of a wide array of linking groups. Alternatively, the linker may be a single bond or a "zero order linker."

Said linker molecule is advantageously a homobifunctional or heterobifunctional molecule, for example adipic dihydrazide, ethylenediamine, cystamine, N-succinimidyl-3-(2-pyridyldithio)propionate (SPDP), N-succinimidyl-[4N-(2-iodoacetyl)]-β-alanyl propionate-propionate (SIAP), succinimidyl-4-(N-maleimido-methyl)cyclohexane-1 carboxylate (SMCC), 3,3'-dithiodipropionic acid. In certain aspects the linker or spacer is a water-soluble polymer, and in one embodiment, the water-soluble polymer comprises poly(ethylene glycol).

II. IMMUNOGENIC COMPOSITIONS AND USES THEREOF

One reason that a glycan-based vaccine against ChD has thus far been elusive is the lack of an adequate animal model closely mimicking the human anti-glycan immune response to $T.$ $cruzi$. One example of a glycan-based epitope is Galα(1,3)Galβ(1,4)GlcNAcα (Galα3LNα or Galα3LN). In certain aspect Galα3LN induces anti-α-Gal Abs. Except for humans and Old World monkeys, mice and all other mammals express this glycan on their cells and are, therefore, tolerant to the epitope. It is reasonable to assume then that the immune response observed in experimental vaccination with Galα-containing immunogens using any regular mouse model (e.g., BALB/c) would not account for the major protective humoral response against the parasite, i.e., Ch anti-α-Gal Abs. Accordingly, most if not all experimental vaccine studies using regular mouse models have been biased towards an almost exclusively CD8+ T cell-mediated protection. In part, this accounts for the fact that the overwhelming majority of experimental $T.$ $cruzi$ vaccines have employed CD8+ T cell epitopes. To circumvent this problem, α1,3GalT-KO mice were used that, like humans and Old World monkeys, do not express Galα1,3Gal epitopes on their cells due to the knock out of the enzyme alpha-1,3-galactosyltransferase. Therefore, the α1,3GalT-KO mouse model mimics humans in regard to the humoral (B cell-mediated) immune response against $T.$ $cruzi$.

An "antigenic determinant" is, unless otherwise indicated, a molecule that is able to elicit an immune response in a particular animal or species. Antigenic determinants include, for example, carbohydrate moieties, such as glycans. In certain aspects an antigenic determinant that is a carbohydrate can be referred to as a "glycotope".

Certain embodiments are directed to immunogenic compositions and methods comprising a Galα3LN conjugate. A Galα3LN conjugate is peptide or protein that has one or more Galα3LN moieties covalently attached, either directly or by a linker.

As used herein, "prophylactic" and "preventive" vaccines are vaccines that are designed and administered to prevent infection, disease, and/or any related sequela(e) caused by or associated with a pathogenic organism, such as a trypanosome or other parasite.

As used herein, "therapeutic" vaccines are vaccines that are designed and administered to patients already infected with a pathogenic organism. Therapeutic vaccines (e.g., therapeutic trypanosome vaccines) are used to prevent and/or treat the development of disease in these infected individuals.

As used herein the phrase "immune response" or its equivalent "immunological response" refers to a humoral (antibody-mediated), cellular (mediated by antigen-specific T cells or their secretion products) or both humoral and cellular response directed against an epitope of the invention in a subject or a donor subject. A donor subject is one in which an antibody is generated and isolated, the isolated antibody is then administered to a second subject. Treatment or therapy can be an active immune response induced by administration of immunogen or a passive therapy affected by administration of antibody, antibody-containing material, or vaccine-primed B and/or T cells.

For purposes of this specification and the accompanying claims the terms "epitope" and "antigenic determinant" are used interchangeably to refer to a site on an antigen to which B and/or T cells respond or recognize.

Embodiments described herein include methods for preventing or ameliorating parasite infections. As such, the invention contemplates vaccines for use in both active and passive immunization embodiments. Immunogenic compositions, proposed to be suitable for use as a vaccine, may be prepared from immunogenic glycans and glycan conjugates.

Typically, such vaccines are prepared as injectables, either as liquid solutions or suspensions: solid forms suitable for solution in or suspension in liquid prior to injection may also be prepared. The preparation may also be emulsified. The active immunogenic ingredient is often mixed with excipients that are pharmaceutically acceptable and compatible with the active ingredient. Suitable excipients are, for example, water, saline, dextrose, glycerol, ethanol, or the like and combinations thereof. In addition, if desired, the vaccine may contain amounts of auxiliary substances such as wetting or emulsifying agents, pH buffering agents, or adjuvants that enhance the effectiveness of the vaccines.

Vaccines may be conventionally administered parenterally, by injection, for example, either subcutaneously or intramuscularly. Formulations can include such normally employed excipients and contain about 10% to about 95% of active ingredient, preferably about 25% to about 70%.

The glycans and glycan-conjugates may be formulated into a vaccine as neutral or salt forms. Pharmaceutically-acceptable salts include the acid addition salts (formed with the free amino groups of the peptide) and those that are formed with inorganic acids such as, for example, hydrochloric or phosphoric acids, or such organic acids as acetic, oxalic, tartaric, mandelic, and the like.

Typically, vaccines are administered in a manner compatible with the dosage formulation, and in such amount as will be therapeutically effective and immunogenic. The quantity to be administered depends on the subject to be treated, including the capacity of the individual's immune system to synthesize antibodies and the degree of protection desired. Precise amounts of active ingredient required to be administered depend on the judgment of the practitioner. However, suitable dosage ranges are of the order of several hundred micrograms of active ingredient per vaccination. Suitable regimes for initial administration and booster shots are also variable, but are typified by an initial administration followed by subsequent inoculations or other administrations.

In certain instances, it will be desirable to have multiple administrations of the vaccine, e.g., 2, 3, 4, 5, 6 or more administrations. The vaccinations can be at 1, 2, 3, 4, 5, 6, 7, 8, to 5, 6, 7, 8, 9, 10, 11, and 12 week intervals, including all ranges there between. Periodic boosters at intervals of 1-5 years will be desirable to maintain protective levels of the antibodies. The course of the immunization may be followed by assays for antibodies against the antigens.

Carriers. A given composition may vary in its immunogenicity. It is often necessary therefore to boost the host immune system, as may be achieved by coupling an antigen to a carrier. An example of carriers are keyhole limpet hemocyanin (KLH) and bovine serum albumin (BSA). Other albumins such as ovalbumin, mouse serum albumin, human serum albumin, or rabbit serum albumin can also be used as carriers. Means for conjugating an antigen to a carrier protein are well known in the art and include glutaraldehyde, m-maleimidobencoyl-N-hydroxysuccinimide ester, carbodiimyde, and bis-biazotized benzidine.

Adjuvants. The immunogenicity of a composition can be enhanced by the use of non-specific stimulators of the immune response, known as adjuvants. Suitable adjuvants include all acceptable immunostimulatory compounds, such as cytokines, toxins, or synthetic compositions. A number of adjuvants can be used to enhance an antibody response against an antigen. Adjuvants can (1) trap the antigen in the body to cause a slow release; (2) attract cells involved in the immune response to the site of administration; (3) induce proliferation or activation of immune system cells; or (4) improve the spread of the antigen throughout the subject's body.

Adjuvants include, but are not limited to, oil-in-water emulsions, water-in-oil emulsions, mineral salts, polynucleotides, and natural substances. Specific adjuvants that may be used include IL-1, IL-2, IL-4, IL-7, IL-12, γ-interferon, GMCSP, BCG, aluminum salts, such as aluminum hydroxide or other aluminum compound, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM), and cell wall skeleton (CWS) in a 2% squalene/Tween 80 emulsion.

Various methods of achieving adjuvant affect for the vaccine includes use of agents such as aluminum hydroxide or phosphate (alum), commonly used as about 0.05 to about 0.1% solution in phosphate buffered saline, admixture with synthetic polymers of sugars (Carbopol®) used as an about 0.25% solution, aggregation of the protein in the vaccine by heat treatment with temperatures ranging between about 70° to about 101° C. for a 30-second to 2-minute period, respectively. Aggregation by reactivating with pepsin-treated (Fab) antibodies to albumin; mixture with bacterial cells (e.g., *C. parvum*), endotoxins or lipopolysaccharide components of Gram-negative bacteria; emulsion in physiologically acceptable oil vehicles (e.g., mannide mono-oleate (Aracel A)); or emulsion with a 20% solution of a perfluorocarbon (Fluosol-DA®) used as a block substitute may also be employed to produce an adjuvant effect.

In addition to adjuvants, it may be desirable to co-administer biologic response modifiers (BRM) to enhance immune responses. BRMs have been shown to upregulate T cell immunity or downregulate suppressor cell activity. Such BRMs include, but are not limited to, Cimetidine (CIM; 1200 mg/d) (Smith/Kline, PA); or low-dose Cyclophosphamide (CYP; 300 mg/m2) (Johnson/Mead, NJ) and cytokines such as γ-interferon, IL-2, or IL-12 or genes encoding proteins involved in immune helper functions, such as B-7.

III. EXAMPLES

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Synthesis of Neoglycoproteins

A. Results and Discussion

Figure 6:
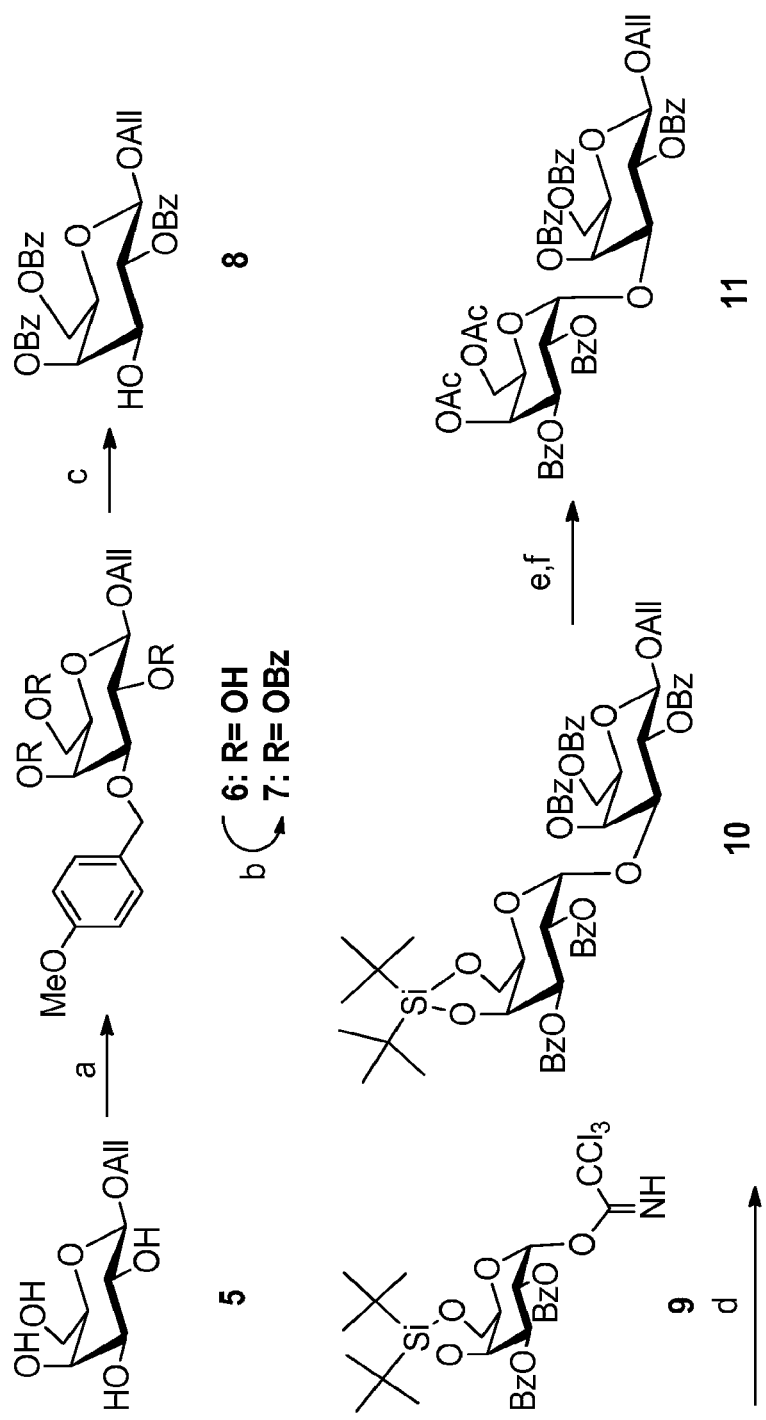
FIG. 6. Illustration of Scheme 1. Synthesis of disaccharide 11. (a) Bu$_2$SnO, MeOH, reflux; 4-OMe-benzyl-Cl (PMBCl), Bu$_4$NBr, benzene, reflux (75%); (b) BzCl, pyr (91%); (c) DDQ, CH$_2$Cl$_2$/H$_2$O (98%); (d) TMSOTf, DCM, 0° C., 4 Å molecular sieves (92%); (e) HF-pyr, THF; (f) Ac$_2$O, pyr (89%, 2 steps).

The α-Gal-containing disaccharide 11 was synthesized from the known allyl (β-galactoside 5 (Stevenson and Furneaux, 1996), which was made from its peracetylated precursor following an optimized procedure (Khamsi et al., 2012). Disaccharide 11 was synthesized in a 55% overall yield, starting with p-methoxybenzylation of allyl glycoside 5 at position 3 via its tin acetal to give 6, followed by benzoylation of the three remaining hydroxyls to afford 7. Oxidative cleavage of the p-methoxybenzyl group with 2,3-dichloro-5,6-dicyano-1,4-benzoquinone furnished the β-Gal acceptor 8. This acceptor was glycosylated with the known di-tert-butylsilylidene equipped α-Gal trichloroacetimidate donor 9 (Imamura et al., 2006), using trimethylsilyl trifluoromethanesulfonate catalysis to give disaccharide 10. The di-tert-butylsilylidene group was cleaved with a large excess of 70% hydrogen fluoride in pyridine in THF, followed by acetylation of the two hydroxyls to give the peracylated allyl disaccharide 11 (FIG. 6, Scheme 1).

Figure 7:
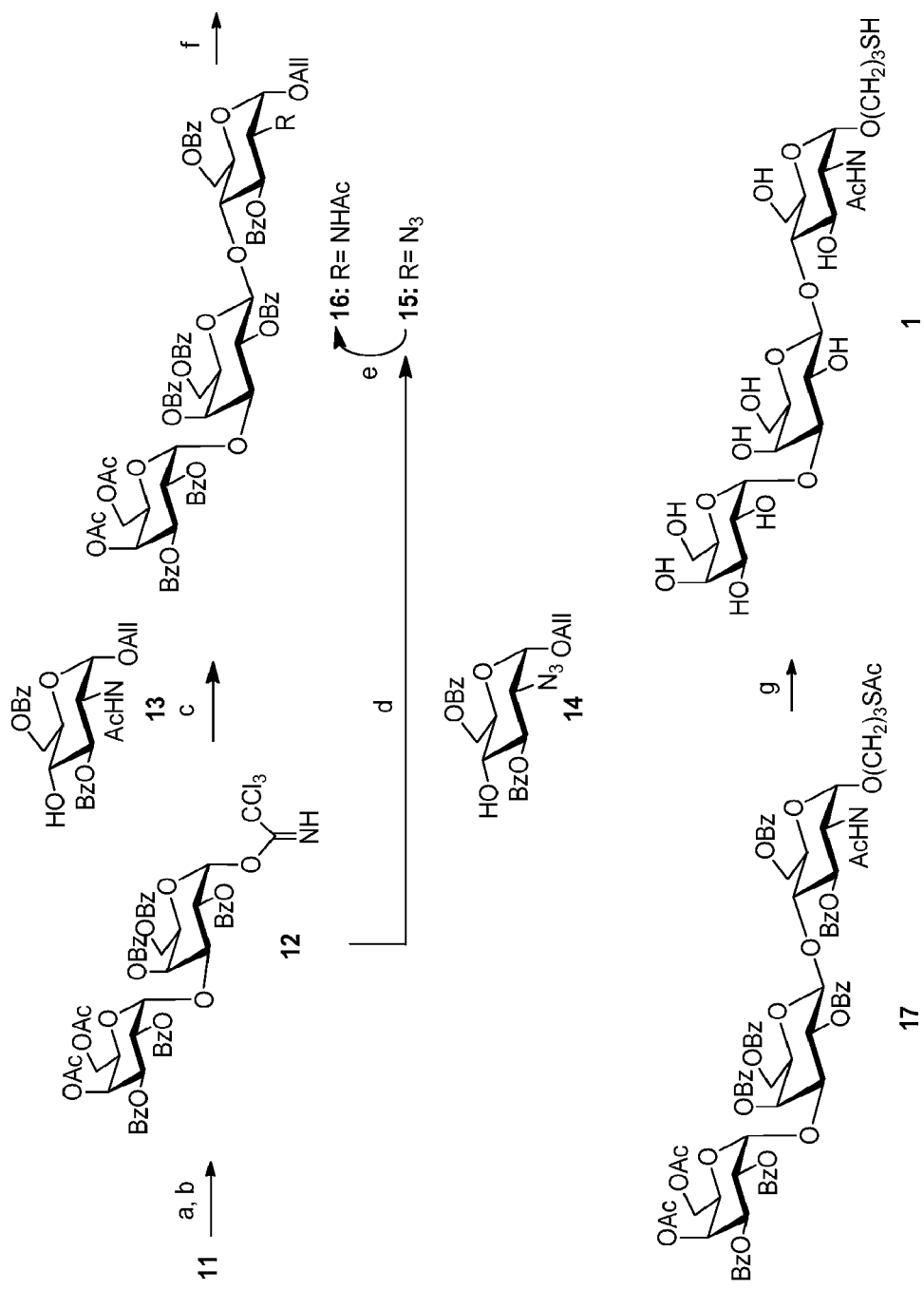
FIG. 7. Illustration of Scheme 2. Synthesis of mercaptopropyl trisaccharide 1. (a) PdCl$_2$, MeOH (87%); (b) CCl$_3$CN, DBU, CH$_2$Cl$_2$ (84%); (c) TMSOTf, molecular sieves 4 Å, CH$_2$Cl$_2$ (30% of 1:4 α/β anomers, FPLC separable); (d) TMSOTf, 4 Å molecular sieves, CH$_2$Cl$_2$ (46%); (e) AcSH (77%); (f) AcSH, AIBN, THF, UV (89%); (g) NaOMe, MeOH (quant.).

The α-Gal-containing disaccharide 11 was then treated with palladium (II) chloride in methanol to give the hemiacetal, which was filtered immediately after consumption of the starting material to avoid the formation of a polar by-product that was observed after two hours of reaction, and converted into the trichloroacetimidate 12 with trichloroacetonitrile in the presence of 1,8-diazabicycloundec-7-ene (FIG. 7, Scheme 2). This donor was first used to glycosylate the allyl GlcNAc acceptor 13 with TMS-OTf, but produced a low-yielding mixture of anomers (1:4 α/β) likely due to the well-known poor nucleophilicity of the 4-OH of GlcNAc acceptors (Crich and Dudkin, 2001). The separation of the two diastereomeric trisaccharides proved to be difficult but could be accomplished by reversed phase FPLC. Replacing the acceptor 13 by the allyl 2-deoxy-2-azido-Glc acceptor 14 produced trisaccharide 15 in 46% yield, which could be purified by flash chromatography, and the azide was then reduced to an N-acetyl group with neat thioacetic acid to give the trisaccharide 16. Radical addition of thioacetic acid with azobisisobutyronitrile in tetrahydrofuran under UV light gave the thioester 17, followed by saponification under Zemplen conditions to afford the target trisaccharide 1 (FIG. 7, Scheme 2).

Figure 8:
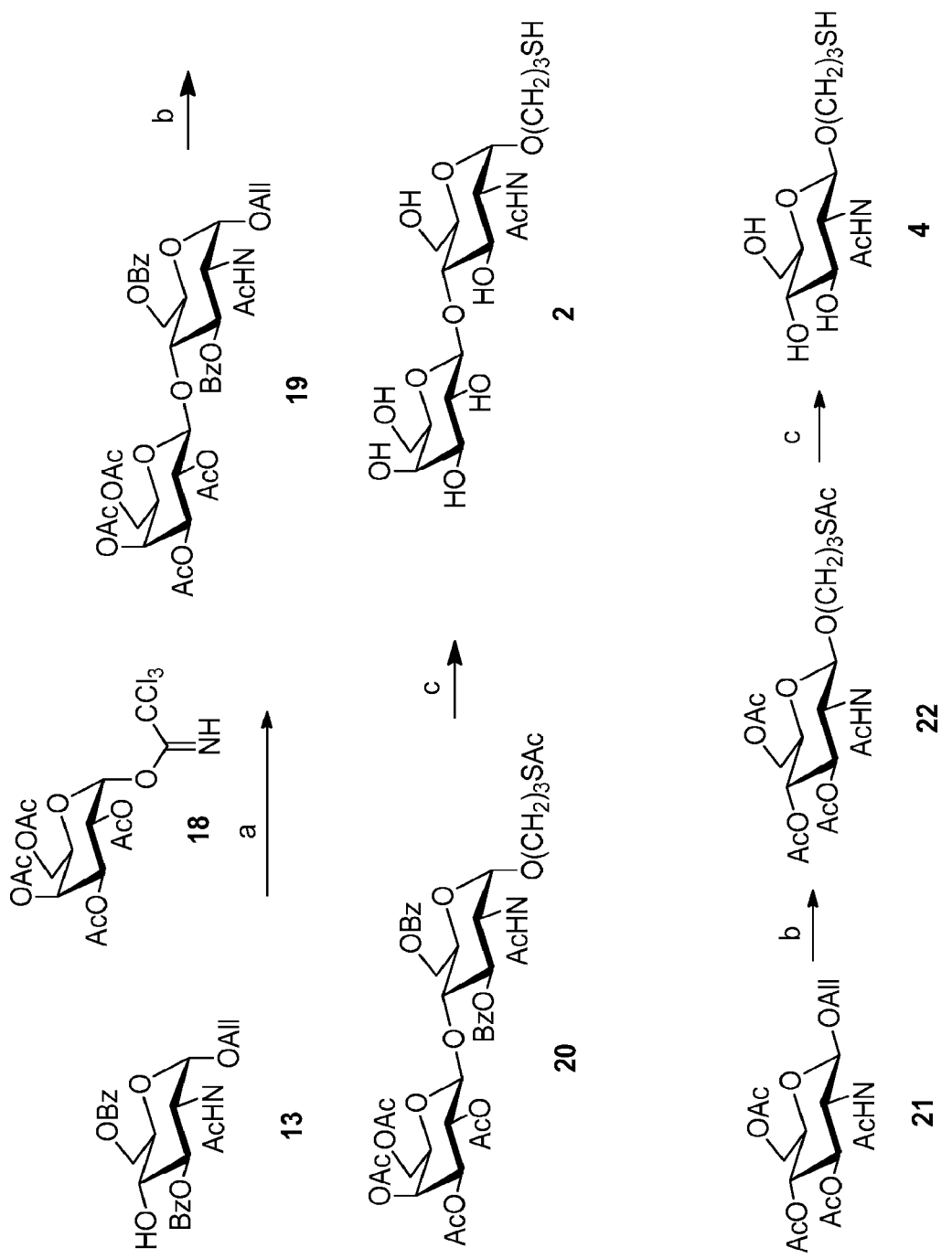
FIG. 8. Illustration of Scheme 3. Synthesis of mercaptopropyl glycosides 2 and 4. (a) BF$_3$-Et$_2$O, CH$_2$Cl$_2$, 35-40° C. (83%); (b) AcSH, AIBN, THF, UV (84-85%); (c) NaOMe, MeOH (quant.).

The Galβ(1,4)GlcNAcα disaccharide 2 was synthesized as shown in FIG. 8 (Scheme 3) in a 70% overall yield from the allyl GlcNAc acceptor 13. Through the use of a large excess of the known acetylated trichloroacetimidate β-Gal donor 18 (Schmidt and Michel, 1980), and the use of boron trifluoride etherate at an unusual elevated temperature (Hendel et al., 2009), the Galβ(1,4)GlcNAcα disaccharide 19 was obtained in high yield (83%), followed by radical addition of thioacetic acid to give the thioester 20. Saponification under Zemplen conditions cleanly gave the target disaccharide 2. The mercaptopropyl glycoside of GlcNAcα (3) was synthesized as previously described (Houseman et al., 2003), while the mercaptopropyl glycoside of GlcNAcβ(4) was synthesized by radical addition of thioacetic acid to the known allyl glycoside 21 (Kiso and Anderson, 1979) to give thioester 22, followed by saponification to provide the target glycoside 4 (FIG. 8, Scheme 3).

Figure 2:
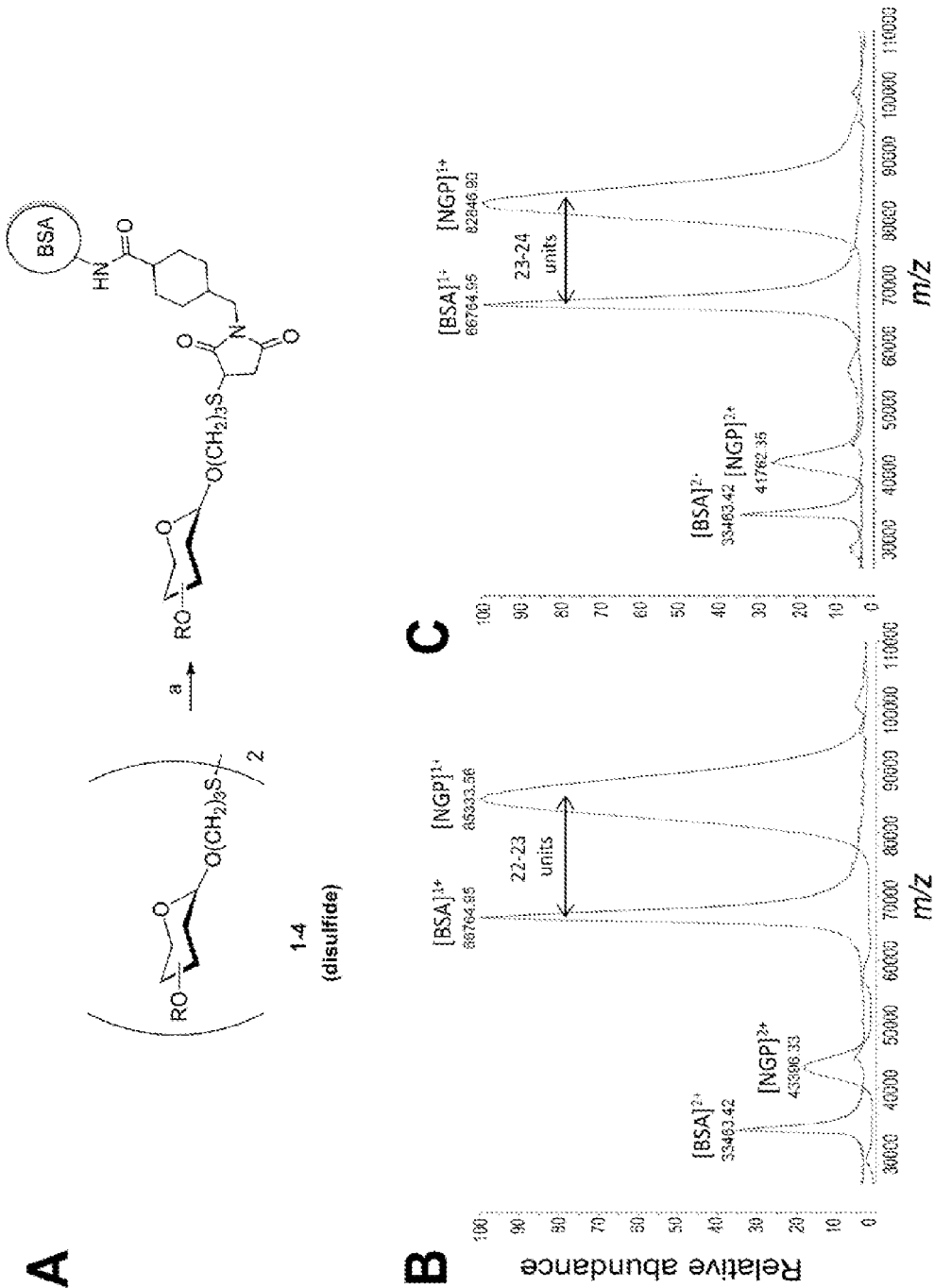
FIG. 2. Scheme of conjugation of neoglycoproteins to BSA (A). (a) tris-(2-carboxyethyl)phosphine, phosphate buffer pH 7.2 and maleimide-activated BSA. Matrix-assisted laser desorption ionization-time of flight mass spectra of Galα(1,3)Galβ(1,4)GlcNAcα-BSA (B) and Galβ(1,4)GlcNAcα-BA (C).

The mercaptopropyl glycosides oxidized to disulfides within hours-days of isolation, which could easily be reduced by tris(2-carboxyethyl)phosphine before their conjugation to BSA. The thiol groups on compounds 1-4 served as nucleophiles in the conjugate addition to commercially available maleimide-derivatized BSA in aqueous buffer at pH 7.2, as shown in FIG. 2. This produced neoglycoproteins via thioether linkages, and the average number of saccharides conjugated per BSA molecule was estimated by matrix-assisted laser desorption ionization-time of flight mass spectrometry. The conjugation of 22-23 units of Galα(1,3)Galβ(1,4)GlcNAcα and 23-24 units of Galβ(1,4)GlcNAcα per molecule of BSA are shown in FIG. 2. An average of 29 units of GlcNAcα and 25 units of GlcNAcβ were conjugated to BSA.

Figure 3:
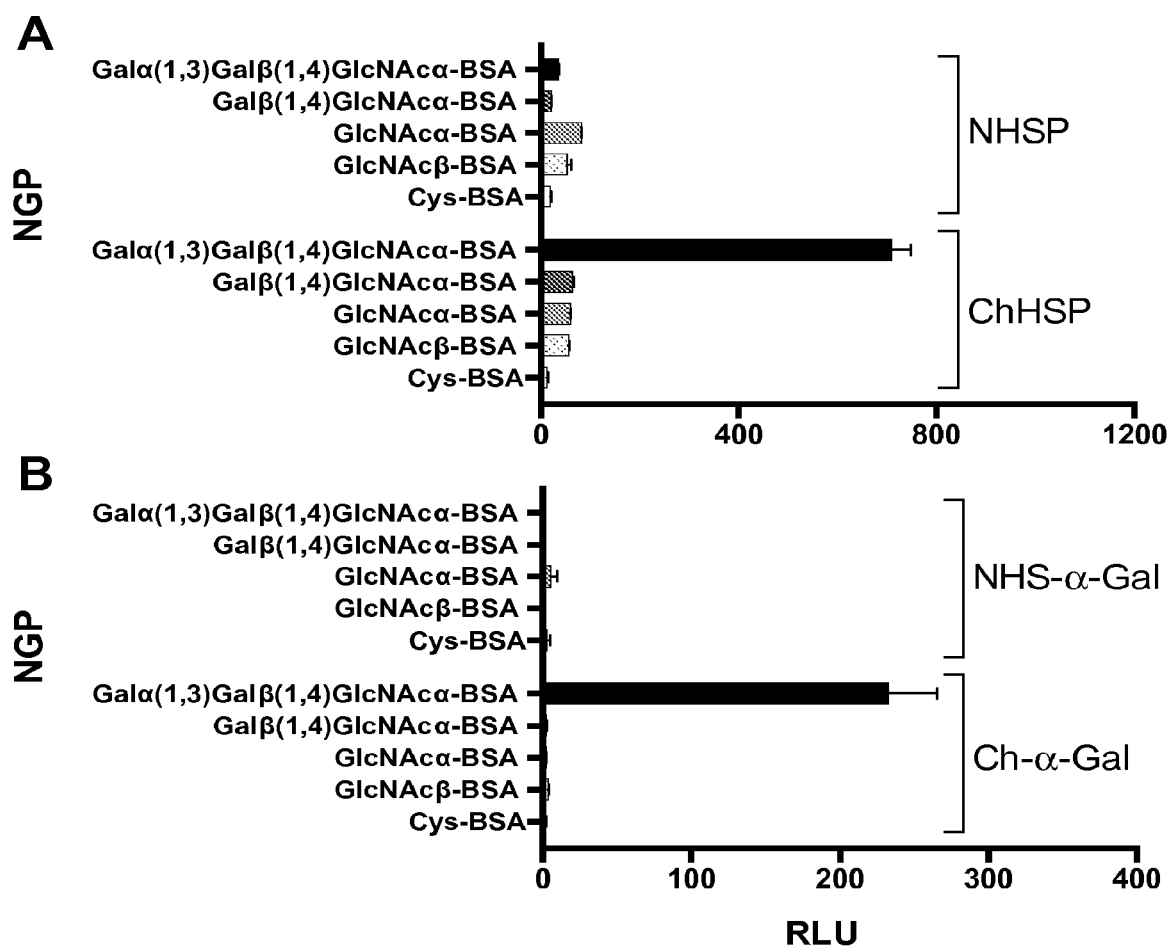
FIG. 3. (A) CL-ELISA reactivity of normal human sera pool (NHSP) vs Chagasic human sera pool (ChHSP) to neoglycoproteins (NGP). (B) CL-ELISA reactivity of purified normal human sera anti-α-Gal Abs (NHS anti-α-Gal) vs Chagasic anti-α-Gal Abs (Ch anti-α-Gal) to neoglycoproteins. RLU, Relative luminescence units.

The four NPGs Galα(1,3)Galβ(1,4)GlcNAcα-BSA, Galβ(1,4)GlcNAcα-BSA, GlcNAcα-BSA, GlcNAcβ-BSA, and a BSA control conjugate in which the maleimide groups had been blocked with cysteine (Cys-BSA), were immobilized in 96-well polystyrene Nunc Maxisorp ELISA plates and antibody-binding responses were measured using CL-ELISA (Almeida et al. 1997), with pooled Chagasic human sera (ChHSP) and normal human sera (NHSP), as well as Ch anti-α-Gal Abs and NHS anti-α-Gal Abs, purified as described (Almeida et al. 1991). As shown in FIG. 3A, Galα(1,3)Galβ(1,4)GlcNAcα-BSA clearly displays a 20-fold differential between ChHSP and NHSP, whereas the NGPs Galβ(1,4)GlcNAcα-BSA, GlcNAcα-BSA, and GlcNAcβ-BSA all show minimal binding to either pooled sera. There was no significant difference between the weak antibody reactivity observed with GlcNAcα and GlcNAcβ. Cys-BSA proved to be an effective negative control. As shown in FIG. 3B, Galα(1,3)Galβ(1,4)GlcNAcα-BSA displays a 230-fold differential between purified Ch and NHS anti-α-Gal antibodies, while neoglycoproteins Galβ(1,4)GlcNAcα-BSA, GlcNAcα-BSA, GlcNAcβ-BSA are practically not recognized by either antibodies. These results emphasize that the terminal Galα residue is crucial for Chagasic antibody binding, and demonstrates a convenient method to differentiate between *T. cruzi*-infected and non-infected sera. In addition, they show that, although Galβ(1,4)GlcNAcα and GlcNAcα are non-self glycotopes for humans, there is little or no antibody response against them in the sera of Chagasic patients (FIG. 3A).

Figure 4:
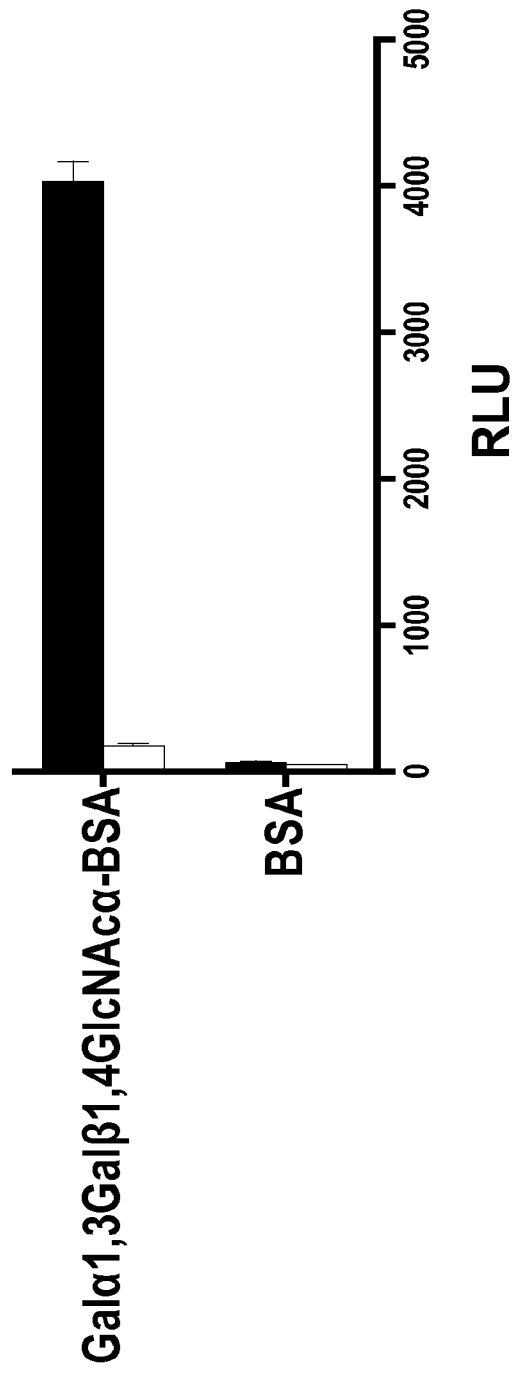
FIG. 4. CL-ELISA reactivity of α1,3GalT-KO mouse serum to the neoglycoprotein Galα(1,3)Galβ(1,4)GlcNAcα-BSA and BSA before (□) and after (■) immunization with the neoglycoprotein or BSA (control).

Next, the in vivo response to Galα(1,3)Galβ(1,4)GlcNAcα-BSA was evaluated in C57Bl/6 α1,3galactosyltransferase-knockout (α1,3GalT-KO) mice. Akin to humans and in contrast to wild-type mice, these animals lack terminal Galα1,3-linked residues on glycoproteins, thus being able to produce high levels of anti-α-Gal antibodies (Tearle et al., 1996; Thall et al., 1996). Sera collected from immunized and control animals were pooled separately and analyzed by CL-ELISA (Ashmus et al., 2013). As shown in FIG. 4, sera from the Galα(1,3)Galβ(1,4)GlcNAcα-BSA-immunized mice displayed a 22-fold higher antibody response to Galα(1,3)Galβ(1,4)GlcNAcα-BSA after immunization as compared to pre-immunization levels, whereas mice immunized with BSA alone showed minimal antibody reactivity before and after immunization.

Figure 5:
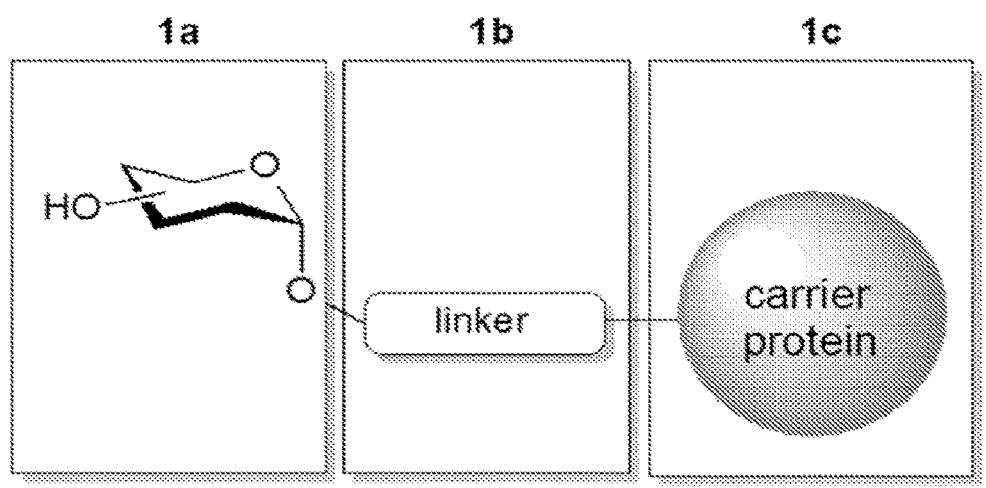
FIG. 5. Illustrates the general structure of neoglycoconjugate vaccine and diagnostic and prognostic (chemotherapy follow-up) biomarkers for Chagas disease and other parasitic diseases. (A and B) Schematic representations of neoglycoconjugates 1 and 2, respectively. Both neoglycoconjugates are composed of the three components as indicated. (A) Component 1a: terminal, nonreducing αGal-containing linear or branched O-glycan (where the linear glycan or at least one or more of the branches includes, but it is not restricted to Galα(1,3)Galβ(1,4)GlcNAcα, Galα(1,3)Galβ(1,4)GlcNAcβ, Galα(1,3)Galβ(1,4)Glcα, Galα(1,3)Galβ(1,4)Glcβ, Galα(1,3)Galβ, Galα(1,3)Galα, Galα(1,2)Galβ(1,4)GlcNAcα, Galα(1,2)Galβ(1,4)GlcNAcβ, Galα(1,2)Galβ(1,4)Glcα, Galα(1,2)Galβ(1,4)Glcβ, Galα(1,2)Galβ, Galα(1,2)Galα and other embodiments thereof), with n sugar residues, where n=1-20 residues. Component 1b: sulfur-substituted succinimide or alpha-thio-carbonyl or thio-ether linker or analogues thereof. Component 1c: any nontoxic carrier or adjuvant protein, including but not restricted to bovine serum albumin (BSA), human serum albumin (HSA), keyhole limpet hemocyanin (KLH), ovalbumin (OVA), or tetanus toxoid (TT). (B) Component 2a: terminal, nonreducing αGal-containing N-glycan (linear or branched) with n sugar residues, where n=1-20 sugar residues. Component 2b: asparagine (Asp) or glutamine (Gln) or homologues thereof with longer side chains. Component 2c: any CD4 or CD8 T cell epitope, or a combination of both, containing n amino acid residues, where n=8-40 amino acids.
Figure 5:
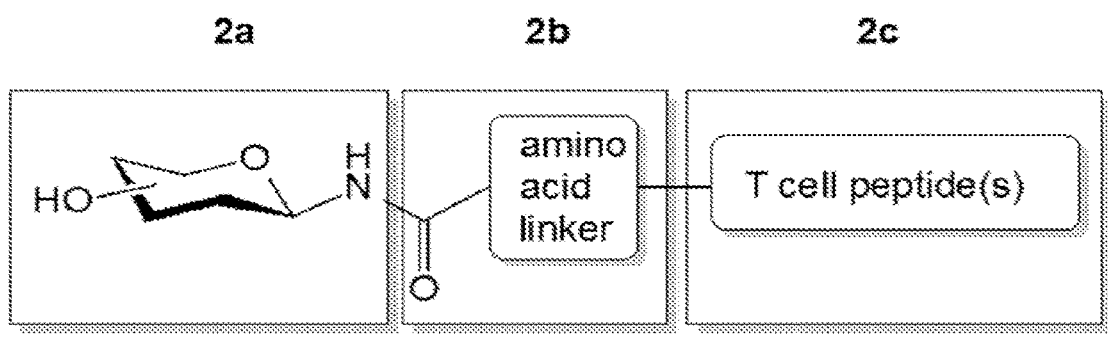

Based on the Galα(1,3)Galβ(1,4)GlcNAcα-BSA neoglycoprotein described above, two series of neoglycoconjugates can be produced, each composed of three components or modules (FIG. 5). The first glycoconjugate is composed of a glycan component (1a), a linker (1b), and a carrier protein (1c) (FIG. 5A). The second glycoconjugate is composed of a glycan component (2a), a linker (2b), and a T-cell peptide (1c) (FIG. 5B). These glycoconjugates could be employed as vaccines, and diagnostic and prognostic (chemotherapy follow-up) biomarkers for Chagas disease (in humans and other mammals, including nonhuman primates) and other parasitic infections, including but not restricted to malaria, leishmaniasis, African trypanosomiasis, and hookworm and tapeworm infections.

The mercaptopropyl glycoside of Galα(1,3)Galβ(1,4)GlcNAcα was efficiently synthesized in 12 steps from known monosaccharide building blocks. In contrast to the published chemical syntheses, this synthesis is the accessibility of the glycosyl acceptors, which are synthesized in 2-3 steps from commercially available starting materials. In addition, the synthesis utilizes common and inexpensive glycosylation catalysts. The two key steps in this synthesis are the stereoselective installation of the terminal Galα unit into disaccharide 10 in 92% yield, and the challenging glycosylation of the 2-deoxy-2-azido acceptor 14 to give the correct stereoisomer (trisaccharide 15) in 46% yield. With the exception of the p-methoxybenzyl group introduced into galactose derivative 6, the di-tert-butylsilylidene protecting group of the galactosyl donor 9, and the allyl group as a precursor of a hemiacetal in compound 11, easily installable and removable acetyl and benzoyl protecting groups were used throughout the synthesis. Utilizing anomeric allyl groups allowed for the convenient conversion into mercaptopropyl glycosides that were needed for the conjugation to maleimide-derivatized BSA. The mercaptopropyl group of these glycosides is highly versatile as it is suitable for the conjugation to a large variety of other biomolecules and surfaces by conjugate addition to maleimides, nucleophilic substitution, and thiol-ene reaction. Finally, the trisaccharide Galα(1,3)Galβ(1,4)GlcNAcα, which is an immunodominant glycotope in infective *T. cruzi* trypomastigotes, is highly immunogenic in the context of *T. cruzi* infection in both mice and humans. It is propose that the Galα(1,3)Galβ(1,4)GlcNAcα-BSA and its analogs containing different carrier proteins or peptides can be further used as diagnostic biomarkers or tools for the diagnosis and follow-up of chemotherapy of ChD, and as vaccine candidates for ChD in humans and nonhuman primates. In addition, these neoglycoconjugates can also be employed as vaccines, and diagnostic and prognostic (chemotherapy follow-up) biomarkers for other parasitic infections, including but not restricted to malaria, leishmaniasis, African trypanosomiasis, and hookworm and tapeworm infections.

B. Materials and Methods

Compound Isolation and characterization. Thin-layer chromatography was performed with silica gel on aluminum support, 8.0-12.0 μm, Sigma-Aldrich, and visualized by UV light or with 2% $H_2SO_4$ in ethanol, followed by heating. Flash chromatography was performed with silica gel, grade A, 32-63 μm, Dynamic Adsorbents. $^1H$ NMR spectra were recorded on a JEOL 600 MHz NMR spectrometer using tetramethylsilane or chloroform as an internal standard. $^{13}C$ NMR spectra were recorded on the same JEOL NMR spectrometer at 150 MHz. Optical rotations were recorded on an Atago AP300 automatic polarimeter. Mass spectra were recorded on a JEOL Accu TOF mass spectrometer using electrospray ionization, or on a Shimadzu Axima MALDI-TOF MS. Dichloromethane and pyridine were refluxed over calcium hydride and distilled, methanol was refluxed over magnesium and distilled. Reagents were purchased from Sigma-Aldrich, Acros Organics, Fisher Scientific, and Alfa Aesar. 96-well polystyrene Nunc MaxiSorp ELISA plates and CL-ELISA reagents were purchased from Thermo Scientific or Jackson ImmunoResearch, luminescence was recorded on a Luminoskan Ascent, Thermo Scientific.

3-thiopropyl α-D-galactopyranosyl-(1→3)-β-D-galactopyranosyl-(1→4)-2-deoxy-2-acetamido-α-D-glucopyranoside (1). To a flask containing 17 (0.027 g, 0.018 mmol), 3 mL of 0.5M NaOMe was added under argon, and stirred at room temperature for 30 minutes. HRMS showed full removal of acyl protecting groups, and all material was present as a mixture of thiol and disulfide. Amberlyst-15 ion-exchange resin was added and stirred until the solution was neutral, followed by filtration through Celite and evaporation of the solvent. The remainder was dissolved in water and lyophilized to give 1 as a white powder (0.011 g, quant.). ESI-TOF HRMS $[C_{23}H_{41}NO_{16}S+Na]^+$ calc. m/z=642.2044, found 642.1980.

3-thiopropyl β-D-galactopyranosyl-(1→4)-2-deoxy-2-acetamido-α-D-glucopyranoside (2). To a flask containing 20 (0.045 g, 0.051 mmol), 4 mL of 0.5M NaOMe was added under argon, and stirred at room temperature for 30 minutes. HRMS showed full removal of acyl protecting groups, and all the material was present as a disulfide. Amberlyst-15 ion-exchange resin was added and stirred until the solution was neutral, followed by filtration through Celite and evaporation of the solvent. The remainder was dissolved in water and lyophilized to give 2 as a white powder (0.024 g, quant.). ESI-TOF HRMS $[C_{34}H_{60}N_2O_{22}S_2+H]^+$ calc. m/z=913.3157, found 913.3046; $[C_{34}H_{60}N_2O_{22}S_{2+}+Na]^+$ calc. m/z=935.2977, found 935.2836.

3-thiopropyl 2-deoxy-2-acetamido-β-D-glucopyranoside (4). To a flask containing 22 (0.059 g, 0.127 mmol), 4 mL of 0.5M NaOMe was added under argon, and stirred at room temperature for 2 hours. HRMS showed full removal of acyl protecting groups, and most of the material was present as a disulfide. Amberlyst-15 ion-exchange resin was added and stirred until the solution was neutral, followed by filtration through Celite and evaporation of the solvent. The remainder was dissolved in water and lyophilized to give 4 as a white powder (0.037 g, quant.). ESI-TOF HRMS $[C_{22}H_{40}N_2O_{12}S_2+Na]^+$ calc. m/z=611.1920, found 611.1707.

Allyl 3-O-(4-methoxybenzyl)-β-D-galactopyranoside (6). A solution of 5 (Stevenson and Furneaux 1996) (0.409 g, 1.86 mmol) and Bu$_2$SnO (0.693 g, 2.79 mmol) in 18 mL anhydrous MeOH was stirred and refluxed under argon for 8 h. The solution was then quickly concentrated, and resuspended in 18 mL benzene. Bu$_4$NBr (0.30 g, 0.93 mmol) was added, followed by 4-methoxybenzyl chloride (0.378 mL, 2.79 mmol), and stirred at 80° C. for 12 h. The solution was concentrated, and purified by column chromatography on silica gel (CHCl$_3$/MeOH 9:1) to give 6 as a white powder (0.430 g, 75%). Its $^1$H and $^{13}$C NMR spectra matched the ones previously described for this compound (Yoshida et al. 2001).

Allyl 3-O-(4-methoxybenzyl)-2,4,6-tri-O-benzoyl-β-D-galactopyranoside (7). A solution of 6 (0.380 g, 1.22 mmol) in 5 mL anhydrous pyridine was cooled to 0° C. under argon. BzCl (0.854 mL, 7.35 mmol) was added dropwise, and stirred for 3 h. The solution was diluted with EtOAc, washed once with 1M HCl, once with a saturated NaHCO$_3$ solution and once with brine, dried over MgSO$_4$, filtered, concentrated, and purified by column chromatography on silica gel (hexanes/EtOAc 2:1) to give 7 as a white powder (0.658 g, 90%). $[α]^{28}{}_D$ 72.4 (c=1 in CHCl$_3$); R$_f$=0.38 (MeOH/CHCl$_3$ 1:9); $^1$H NMR (600 MHz, CDCl$_3$, 300K) δ 8.18; 8.05; 7.97; 7.56-7.61; 7.43-7.50 (5 m, 15H, 3×Bz); 7.05; 6.59 (2 m, 4H, 4-OMe-benzyl); 5.90 (m, 1H, H-4); 5.77 (m, 1H, OCH$_2$CHCH$_2$); 5.55 (dd, 1H, $^3J_{H1/H2}$=8.9 Hz, $^3J_{H2/H3}$=8.9 Hz, H-2); 5.18 (m, 1H, OCH$_2$CHCH$_2$); 5.07 (m, 1H, OCH$_2$'CHCH$_2$); 4.60-4.67 (m, 3H, H-1, H-6, CH$_2$PhOMe); 4.41-4.47 (m, 2H, H-6', CH$_2$'PhOMe); 4.35 (m, 1H, OCH$_2$CHCH$_2$); 4.13 (m, 1H, OCH$_2$CHCH$_2$'); 4.08 (m, 1H, H-5); 3.79 (dd, 1H, $^3J_{H3/H4}$=3.4 Hz, H-3); 3.70 (s, 3H, OCH$_3$) ppm. $^{13}$C NMR (150 MHz, CDCl$_3$, 300K): δ 166.3; 166.0; 165.3; 159.3; 133.7; 133.5; 133.4; 133.1; 130.3; 129.6-130.1; 129.5; 129.4; 128.5-128.7; 128.4; 117.7; 113.7; 100.2 (C-1); 75.8; 71.5; 71.3; 70.7; 70.1; 66.8; 62.8; 55.2 ppm. ESI-TOF HRMS $[C_{38}H_{36}O_{10}+Na]^+$ calc. m/z=675.2206, found 675.2001; $[C_{38}H_{36}O_{10}+K]^+$ calc. m/z=691.1946, found 691.2022.

Allyl 2,4,6-tri-O-benzoyl-β-D-galactopyranoside (8). To a solution of 7 (0.633 g, 0.97 mmol) in 20 mL CH$_2$Cl$_2$ and 1.1 mL H$_2$O, 2,3-dichloro-5,6-dicyano-1,4-benzoquinone (DDQ) (0.440 g, 1.94 mmol) was added in two portions, 30 minutes apart, and stirred vigorously for 12 h. The red and green solution was filtered through Celite, diluted with dichloromethane, and extracted with water (25 mL) and brine solution (25 mL), dried over MgSO$_4$, filtered, concentrated, and purified by column chromatography on silica gel (EtOAc/hexanes 2:1) to give 8 as a white powder (0.504 g, 98%). Its $^1$H and $^{13}$C NMR spectra matched the ones previously described for this compound (Sherman et al. 2001).

Allyl 4,6-di-O-tert-butylsilylene-2,3-di-O-benzoyl-α-D-galactopyranosyl-(1→3)-2,4,6-tri-O-benzoyl-β-D-galactopyranoside (10). A solution of acceptor 8 (0.175 g, 0.329 mmol) and 4,6-di-O-tertbutylsilyl-2,3-di-O-benzoyl-α-D-galactopyranosyl trichloroacetimidate donor 9 (Imamura et al. 2006) (0.266 g, 0.395 mmol) in anhydrous dichloromethane (6 mL) was added to a 10 mL round bottomed flask with freshly activated, crushed 4 Å molecular sieves and stirred under argon for 15 min. at 0° C. TMSOTf (0.010 mL, 0.059 mmol) was added dropwise, and the mixture was gradually brought to room temperature and stirred for 2 h. To quench the reaction, Et$_3$N (0.010 mL, 0.072 mmol) was added and stirred. The solution was diluted with dichloromethane (50 mL) and extracted with water (2×25 mL) and brine solution (25 mL), dried over MgSO$_4$, filtered, concentrated, and purified by column chromatography on silica gel (hexanes/EtOAc 3:1) to give 10 as a white powder (0.315 g, 92%). $[α]^{28}{}_D$ 160.7 (c=1 in CHCl$_3$); R$_f$=0.55 (EtOAc/hexanes 1:2); $^1$H NMR (600 MHz, CDCl$_3$, 300K) δ 8.09, 7.99, 7.84, 7.74, 7.60, 7.51, 7.41, 7.26, 7.13, 7.01 (10 m, 25H, 5×Bz); 5.79-5.87 (m, 2H, OCH$_2$CHCH$_2$, βGalH-4); 5.70-5.76 (m, 2H, αGalH-2, βGalH-2); 5.62 (d, 1H, $^3J_{H1/H2}$=3.4 Hz, αGalH-1); 5.26 (m, 1H, OCH$_2$CHCH$_2$); 5.16 (m, 2H, OCH$_2$'CHCH$_2$, αGalH-3); 4.77 (d, 1H, $^3J_{H1/H2}$=8.3 Hz, βGalH-1); 4.55 (dd, 1H, $^3J_{H5/H6}$=11.7 Hz, $^2J_{H6/H6}$=6.9 Hz, βGalH-6); 4.40 (m, 1H, OCH$_2$CHCH$_2$); 4.22-4.30 (m, 3H, βGalH-3, βGalH-5, αGalH-4); 4.19 (m, 1H, OCH$_2$CHCH$_2$'); 4.03-4.14 (m, 2H, αGalH-5, βGalH-6'); 3.64-3.71 (m, 2H, αGalH-6, αGalH-6'); 1.02 (s, 9H, t-butyl); 0.79 (s, 9H, t-butyl) ppm. $^{13}$C NMR (150 MHz, CDCl$_3$, 300K): δ 166.3, 166.1, 165.6, 165.4, 165.0, 133.6, 133.4; 133.4; 133.0; 132.9; 132.8; 129.5-129.9; 129.2; 128.8; 128.6; 128.3; 128.1; 118.0; 100.3 (βC-1); 94.2 (αC-1); 73.8; 71.5; 70.9; 70.7; 70.5; 70.2; 67.6; 67.1; 66.5; 65.9; 62.3; 27.4; 27.2; 25.4; 23.2; 20.7 ppm. ESI-TOF HRMS $[C_{58}H_{62}O_{16}Si+Na]^+$ calc. m/z=1065.3705, found 1065.3587; $[C_{58}H_{62}O_{16}Si+K]^+$ calc. m/z=1081.3444, found 1081.2728.

Allyl 2,3-di-O-benzoyl-4,6-di-O-acetyl-α-D-galactopyranosyl-(1→3)-2,4,6-tri-O-benzoyl-β-D-galactopyranoside (11). A solution of 10 (0.464 g, 0.444 mmol) in anhydrous THF (7 mL) was added to a 50 mL plastic conical tube and stirred under argon at rt. A solution of HF-pyridine (70% HF, 30% pyridine) (0.223 mL, 8.88 mmol) was added to the reaction mixture and stirred for 3 h, then quenched with 0.5 mL saturated NaHCO$_3$. The solution was diluted with EtOAc and extracted with water and brine, dried over MgSO$_4$, and concentrated. The compound was then added to a 25 mL round bottom flask in 5 mL anhydrous pyridine, and Ac$_2$O was added (0.252 mL; 2.66 mmol) and stirred for 12 h. The solvent was then co-evaporated with toluene, and the remainder was purified by column chromatography on silica gel (hexanes/EtOAc 2:1) to give 11 as a white powder (0.389 g, 89% in 2 steps). $[\alpha]^{28}{}_D$ 163.0 (c=1 in CHCl$_3$); $R_f$=0.20 (EtOAc/hexanes 1:2); $^1$H NMR (600 MHz, CDCl$_3$, 300K) δ 8.15; 7.99; 7.70; 7.61; 7.51; 7.44; 7.39; 7.28; 7.24; 7.10; 7.01 (11 m, 25H, 5×Bz); 5.80-5.86 (m, 2H, OCH$_2$CHCH$_2$, βGalH-4); 5.76 (dd, 1H, $^3J_{H2/H3}$=9.6 Hz, βGalH-2); 5.67 (d, 1H, $^3J_{H1/H2}$=4.1 Hz, αGalH-1); 5.61 (dd, 1H, $^3J_{H2/H3}$=11.0 Hz, αGalH-2); 5.41 (dd, 1H, $^3J_{H3/H4}$=3.4 Hz, αGalH-3); 5.26 (m, 1H, OCH$_2$CHCH$_2$); 5.09-5.17 (m, 2H, OCH$_2$'CHCH$_2$, αGalH-4); 4.78 (d, 1H, $^3J_{H1/H2}$=7.6 Hz, βGalH-1); 4.57 (dd, 1H, $^3J_{H5/H6}$=11.0 Hz, $^2J_{H6/H6'}$=6.2 Hz, βGalH-6); 4.41 (m, 1H, OCH$_2$CHCH$_2$); 4.27-4.32 (m, 2H, βGalH-3, βGalH-5); 4.19 (m, 2H, OCH$_2$CHCH$_2$', αGalH-5); 4.11 (dd, 1H, $^3J_{H5/H6}$=6.6 Hz, βGalH-6'); 3.96 (m, 2H, αGalH6, αGalH6'); 1.97-2.03 (m, 6H, 2×Ac) ppm. $^{13}$C NMR (150 MHz, CDCl$_3$, 300K): δ 170.1; 169.8; 166.2; 166.0; 165.4; 165.1; 164.9; 133.6; 133.5; 133.4; 133.1; 133.0; 129.8; 129.8; 129.7; 129.5; 129.5; 129.3; 128.8; 128.6; 128.4; 128.3; 128.3; 128.2; 118.1; 100.3 (βC-1); 93.4 (αC-1); 73.4; 71.5; 70.6; 70.2; 67.9; 67.6; 66.8; 65.5; 62.3; 61.5; 20.8; 20.6 ppm. ESI-TOF HRMS [C$_{54}$H$_{50}$O$_{18}$+NH$_4$]$^+$ calc. m/z=1004.3341, found 1004.3070.

Trichloroacetimidate 2,3-di-O-benzoyl-4,6-di-O-acetyl-α-D-galactopyranosyl-(1→3)-2,4,6-tri-O-benzoyl-β-D-galactopyranoside (12). To a solution of 11 (0.369 g, 0.374 mmol) in MeOH (6 mL), PdCl$_2$ (0.0398 g, 0.225 mmol) was added and stirred for 2 h at room temperature until consumption of most of the starting material. After 2 h, a degradation product can be observed. The solution was filtered through Celite, concentrated, and purified by column chromatography on silica gel (EtOAc/hexanes 2:3) to give the α and β anomers (0.308 g, 87%). A recovered compound assumed to be remaining starting material was actually the vinyl glycoside. The anomeric product mixture was then placed into a round-bottomed flask, 10 mL anhydrous CH$_2$Cl$_2$ was added under argon, and the solution was cooled to 0° C. CCl$_3$CN (0.325 mL, 3.24 mmol) was added, followed by dropwise addition of DBU (0.015 mL, 0.097 mmol) and the mixture was brought to rt over 3 h. The solution was concentrated and purified by column chromatography on silica gel (EtOAc/hexanes 1:2) to give 12 as a white powder (0.295 g, 84%). $[\alpha]^{27}{}_D$ 186.2 (c=1 in CHCl$_3$); $R_f$=0.65 (acetone/hexanes 1:1); $^1$H NMR (600 MHz, CDCl$_3$, 300K) δ 8.64 (s, 1H, NH); 8.10; 7.94; 7.67-7.71; 7.53-7.63; 7.47; 7.36-7.41; 7.23-7.30; 7.12; 7.02 (9 m, 25H, 5×Bz); 6.90 (d, 1H, $^3J_{H1/H2}$=3.4 Hz, αGalH-1) 5.99 (d, 1H, $^3J_{H4/H5}$=2.8 Hz, αGalH-4); 5.94 (dd, 1H, $^3J_{H2/H3}$=10.3 Hz, αGalH-2); 5.76 (d, 1H, $^3J_{H1/H2}$=3.4 Hz, αGal'H-1); 5.65 (dd, 1H, $^3J_{H2/H3}$=10.3 Hz, αGal'H-2); 5.49 (dd, 1H, $^3J_{H3/H4}$=3.4 Hz, αGal'H-3); 5.28 (m, 1H, αGal'H-4); 4.76 (dd, 1H, $^3J_{H3/H4}$=3.4 Hz, αGalH-3); 4.65 (m, 1H, αGalH-5); 4.44 (dd, 1H, 7.6 Hz, 11.7 Hz, αGalH-6); 4.41 (dd, 1H, $^3J_{H5/H6}$=11.7 Hz, αGal'H-5); 4.31 (dd, 1H, 5.5 Hz, 11.7 Hz, αGalH-6'); 4.09-4.14 (m, 1H, αGal'H-6); 4.02 (dd, 1H, $^2J_{H6/H6'}$=6.2 Hz, αGal'H-6'); 1.98-2.06 (m, 6H, 2×Ac) ppm. $^{13}$C NMR (150 MHz, CDCl$_3$, 300K): δ 170.2; 169.8; 166.0; 165.6; 165.3; 165.0; 160.5; 133.9; 133.0-133.3; 129.6-129.9; 129.4; 128.8; 128.5; 128.3; 128.2; 93.8 (αGalC-1); 93.2 (αGal'C-1); 90.9 (CCl$_3$); 70.1; 69.5; 68.7; 67.8; 66.7; 66.0; 62.5; 60.9; 20.9; 20.6 ppm. ESI-TOF HRMS did not show a molecular ion peak for [C$_{53}$H$_{46}$Cl$_3$NO$_{18}$]$^+$.

Allyl 2-deoxy-2-acetamido-3,6-di-O-benzoyl-α-D-glucopyranoside (13). To a solution of allyl 2-deoxy-2-acetamido-α-D-glucopyranoside (Gavard et al. 2003) (3.98 g, 15.24 mmol) in 80 mL anhydrous AcCN, 1-benzoylimidazole (5.46 mL, 36.56 mmol) was added via a plastic syringe, and was heated at 80° C. for 12 h. After evaporation of the solvent the remainder was dissolved in EtOAc and extracted twice with water and once with brine solution, dried over MgSO$_4$, filtered, concentrated, and purified by column chromatography on silica gel (toluene/EtOAc 2:1) to give 13 as a white powder (4.79 g, 67%). Its $^1$H and $^{13}$C NMR spectra matched the ones previously described for this compound (Danac et al. 2007). A minor byproduct with a higher $R_f$ value was identified as the tri-O-benzoylated compound.

Allyl 2-deoxy-2-azido-3,6-di-O-benzoyl-α-D-glucopyranoside (14). Compound 14 was prepared similarly to a published synthesis with slight variations in the solvent and the time period over which BzCl was added (Danac et al. 2007): A solution of allyl 2-deoxy-2-azido-α-D-glucopyranoside (Gavard et al. 2003) (0.30 g, 1.223 mmol) in 10 mL anhydrous pyridine was cooled to −20° C., and BzCl (0.350 mL, 3.01 mmol) was added dropwise in 3 portions of 0.117 mL each over 1 h, and stirred for an additional 1 h. The solution was diluted with EtOAc and extracted twice with water and once with brine solution, dried over MgSO$_4$, filtered, concentrated, and purified by column chromatography on silica gel (hexanes/EtOAc 5:2) to give 14 as a white powder (0.364 g, 66%). $[\alpha]^{25}{}_D$ 161.0 (c=1 in CHCl$_3$) $R_f$=0.48 (EtOAc/hexanes 1:2); NMR (600 MHz, CDCl$_3$, 300K) δ 8.05-8.11; 7.58; 7.43-7.48 (m, 10H, 2×Bz); 5.95 (m, 1H, OCH$_2$CHCH$_2$); 5.64 (dd, 1H, $^3J_{H3/H4}$=9.6 Hz, H-3); 5.36 (m, 1H, OCH$_2$CHCH$_2$); 5.25 (m, 1H, OCH$_2$'CHCH$_2$); 5.09 (d, 1H, $^3J_{H1/H2}$=4.1 Hz, H-1); 4.73 (dd, 1H, $^3J_{H5/H6}$=4.8 Hz, $^2J_{H6/H6'}$=12.4 Hz, H-6); 4.60 (dd, 1H, $^3J_{H5/H6}$=2.1 Hz, H-6'); 4.29 (m, 1H, CH$_2$CHCH$_2$); 4.12 (m, 2H, H-5, CH$_2$CHCH$_2$'); 3.77 (dd, 1H, $^3J_{H4/H5}$=9.6 Hz, H-4); 3.47-3.54 (broad, 1H, 4-OH); 3.44 (dd, 1H, $^3J_{H2/H3}$=11.0 Hz, H-2) ppm. $^{13}$C NMR (150 MHz, CDCl$_3$, 300K): δ 167.2; 167.0; 133.7; 133.4; 133.0; 130.1; 129.7-130.0; 129.2; 128.6; 128.6; 118.5; 97.0 (C-1); 74.0; 70.7; 70.0; 69.0; 63.5; 61.2 ppm. ESI-TOF HRMS [C$_{23}$H$_{23}$N$_3$O$_7$+H]$^+$ calc. m/z=454.1614, found 454.1912. A minor byproduct of this reaction was identified as the tri-O-benzoylated compound.

Allyl 2,3-di-O-benzoyl-4,6-di-O-acetyl-α-D-galactopyranosyl-(1→3)-2,4,6-tri-O-benzoyl-β-D-galactopyranosyl-(1→4)-2-deoxy-2-azido-3,6-di-O-benzoyl-α-D-glucopyranoside (15). A solution of acceptor 14 (0.126 g, 0.279 mmol) and donor 12 (0.304 g, 0.279 mmol) in anhydrous CH$_2$Cl$_2$ (6 mL) was placed in a 10 mL round bottomed flask with freshly activated, crushed 4 Å molecular sieves and stirred under argon for 15 min at 0° C. TMS-OTf (0.015 mL, 0.0835 mmol) was added dropwise to the reaction mixture, which was gradually brought to room temperature and stirred for 2 h. The reaction was quenched with Et$_3$N (0.02 mL, 0.143 mmol), filtered through Celite, concentrated and purified by column chromatography on silica gel (hexanes/EtOAc 2:1) to give 15 as a slightly yellow powder (0.175 g, 46%). $[\alpha]^{26}{}_D$ 106.1 (c=1 in CHCl$_3$) $R_f$=0.53 (EtOAc/hexanes 1:1); $^1$H NMR (600 MHz, CDCl$_3$, 300K) δ 8.20; 8.02; 7.97; 7.68;

7.55-7.64; 7.36-7.52; 7.31; 7.23; 7.11; 6.97 (10 m, 35H, 7×Bz); 5.93 (m, 1H, OCH$_2$CHCH$_2$); 5.87 (dd, 1H, $^3J_{H2/H3}$=9.5 Hz, $^3J_{H3/H4}$=9.5 Hz, αGlcH-3); 5.66 (dd, 1H, $^3J_{H1/H2}$=9.5 Hz, βGalH-2); 5.56 (m, 1H, βGalH-4); 5.53 (d, 1H, $^3J_{H1/H2}$=3.4 Hz, αGalH-1); 5.34 (m, 1H, OCH$_2$CHCH$_2$); 5.30 (dd, 1H, $^3J_{H2/H3}$=10.3 Hz, αGalH-2); 5.24 (m, 1H, OCH$_2$'CHCH$_2$); 5.06 (d, 1H, $^3J_{H1/H2}$=3.4 Hz, αGlcH-1); 4.95 (m, 1H, αGalH-3); 4.80 (d, 1H, $^3J_{H1/H2}$=7.9 Hz, βGalH-1); 4.53-4.60 (m, 2H, βGalH-6, βGalH-6'); 4.26 (m, 1H, OCH$_2$CHCH$_2$); 4.05-4.18 (m, 5H, OCH$_2$CHCH$_2$, βGalH-3, βGalH-5, αGlcH-4, αGalH-4); 4.01 (m, 1H, αGalH-5); 3.87 (dd, 1H, $^3J_{H5/H6}$=11.0 Hz, $^2J_{H6/H6'}$=6.9 Hz, αGalH-6); 3.82 (dd, 1H, $^3J_{H5/H6}$=11.7 Hz, αGalH-6'); 3.73-3.78 (m, 2H, αGlcH-5, αGlcH-6); 3.40-3.49 (m, 2H, αGlcH-2, αGlcH-6'); 1.95-1.99 (m, 6H, 2×Ac) ppm. $^{13}$C NMR (150 MHz, CDCl$_3$, 300K): δ 170.3; 169.7; 166.0; 165.9; 165.7; 165.2; 164.8; 164.5; 133.8; 133.5; 133.2; 133.0-133.1; 132.9; 129.2-130.0; 128.5-128.9; 128.0-128.4; 118.7; 101.3 (βGalC-1); 96.9 (αGlcC-1); 92.9 (αGalC-1); 76.4; 73.2; 71.3; 70.8; 70.6; 69.1; 69.0; 67.9; 67.8; 67.3; 66.8; 64.6; 62.5; 61.8; 61.4; 61.1; 20.7; 20.5 ppm. ESI-TOF HRMS [C$_{74}$H$_{67}$N$_3$O$_{24}$+Na]$^+$ calc. m/z=1399.4458, found 1399.4391; [C$_{74}$H$_{67}$N$_3$O$_{24}$+K]$^+$ calc. m/z=1420.3752, found 1420.3016.

Allyl 2,3-di-O-benzoyl-4,6-di-O-acetyl-α-D-galactopyranosyl-(1→3)-2,4,6-tri-O-benzoyl-β-D-galactopyranosyl-(1→4)-2-deoxy-2-acetamido-3,6-di-O-benzoyl-α-D-glucopyranoside (16). To a flask containing 15 (0.125 g, 0.0904 mmol), was added 8 mL of thioacetic acid, and was stirred for 24 h at 40° C. The solution was concentrated by two co-evaporations with toluene, and purified by column chromatography on silica gel (EtOAc/hexanes 1:1→3:1) to give 16 as a white powder (0.097 g, 77%). [α]$^{26}_D$ 94.3 (c=1 in CHCl$_3$); R$_f$=0.15 (hexanes/EtOAc 1:1); $^1$H NMR (600 MHz, CDCl$_3$, 300K) δ 8.20; 8.02; 7.96; 7.68; 7.55-7.63; 7.47-7.53; 7.36-7.45; 7.28-7.35; 7.22; 7.15; 7.03; 6.95 (10 m, 35H, 7×Bz); 5.84-5.92 (m, 2H, OCH$_2$CHCH$_2$, NH); 5.52-5.67 (m, 5H, βGalH-2, βGalH-4, αGalH-1, αGlcNAcH-3); 5.26-5.31 (m, 2H, αGalH-2, OCH$_2$CHCH$_2$); 5.23 (m, 1H, OCH$_2$CHCH$_2$); 4.90-4.94 (m, 2H, αGlcNAcH-1, αGalH-3); 4.80 (d, 1H, $^3J_{H1/H2}$=7.6 Hz, βGalH-1); 4.50-4.59 (m, 3H, αGlcNAcH-2); 4.06-4.22 (m, 4H, βGalH-3, OCH$_2$CHCH$_2$); 4.00 (m, 2H, OCH$_2$CHCH$_2$); 3.88 (dd, 1H); 3.78-3.84 (m, 2H); 3.66-3.72 (m, 2H); 1.96-2.00 (m, 6H, 2×Ac); 1.86 (s, 3H, NHAc) ppm. $^{13}$C NMR (150 MHz, CDCl$_3$, 300K): δ 170.3; 170.2; 169.7; 166.6; 166.1; 165.9; 165.7; 165.2; 164.8; 164.6; 133.9; 133.5; 133.3; 133.1; 133.1; 132.9; 130.0; 129.5-129.8; 129.4; 129.2; 128.9; 128.6-128.8; 128.0-128.4; 118.6; 101.3 ((3Ga1C-1); 96.4 (aGlcNAcC-1); 92.9 (aGa1C-1); 75.9; 73.2; 71.7; 71.4; 70.8; 69.0; 68.8; 67.9; 67.8; 67.3; 66.8; 64.6; 62.5; 61.8; 61.1; 52.1; 29.8; 23.3; 20.8; 20.5 ppm. ESI-TOF HRMS [C$_{76}$H$_{71}$NO$_{25}$+H]$^+$ calc. m/z=1398.4393, found 1398.4308; [C$_{76}$H$_{71}$NO$_{25}$+Na]$^+$ calc. m/z=1420.4213, found 1420.4487; [C$_{76}$H$_{71}$NO$_{25}$+K]$^+$ calc. m/z=1436.3935, found 1436.3893.

3-(acetylthio)propyl 2,3-di-O-benzoyl-4,6-di-O-acetyl-α-D-galactopyranosyl-(1→3)-2,4,6-tri-O-benzoyl-β-D-galactopyranosyl-(1→4)-2-deoxy-2-acetamido-3,6-di-O-benzoyl-α-D-glucopyranoside (17). To a solution of 16 (0.030 g, 0.022 mmol) and AIBN (0.004 g, 0.022 mmol) in anhydrous THF (3 mL), thioacetic acid (0.016 mL, 0.222 mmol) was added and stirred under argon for 5 min. The solution was then placed in a Rayonet UV reactor (350 nm) and stirred for 12 h under water cooling (rt). The solution was concentrated by two co-evaporations with toluene, and purified by column chromatography on silica gel (EtOAc/Hex 2:1) to give 17 as a white powder (0.028 g, 89%). [α]$^{26}_D$ 94.2 (c=0.5 in CHCl$_3$); R$_f$=0.48 (EtOAc/hexanes 2:1); $^1$H NMR (600 MHz, CDCl$_3$, 300K) δ 8.20; 8.01; 7.96; 7.68; 7.55-7.63; 7.47-7.53; 7.20-7.45; 7.13; 7.06; 6.95 (10 m, 35H, 7×Bz); 6.19 (d, 1H, $^3J_{H1/H2}$=9.3 Hz, NH); 5.52-5.67 (m, 4H, βGalH-2, αGalH-2); 5.52 (d, 1H, $^3J_{H1/H2}$=3.4 Hz, αGalH-1); 5.28 (dd, 1H, $^3J_{H2/H3}$=10.3 Hz, $^3J_{H3/H4}$=10.3 Hz, αGalH-3); 4.92 (m, 1H, αGalH-4); 4.83 (d, 1H, $^3J_{H1/H2}$=3.4 Hz, αGlcNAcH-1); 4.79 (d, 1H, $^3J_{H1/H2}$=8.3 Hz, βGalH-1); 4.52-4.59 (m, 3H, αGlcNAcH-2); 4.09-4.16 (m, 2H); 4.04 (m, 1H); 4.00 (m, 1H, αGalH-5); 3.87 (dd, 1H, $^3J_{H5/H6}$=11.7 Hz, $^2J_{H6/H6'}$=6.9 Hz, αGalH-6); 3.81 (dd, 1H, $^3J_{H5/H6}$=11.7 Hz, αGalH-6'); 3.68-3.78 (m, 3H, OCH$_2$CH$_2$CH$_2$); 3.62 (dd, 1H, OCH$_2$CH$_2$CH$_2$); 3.09 (m, 1H, OCH$_2$CH$_2$CH$_2$); 2.95 (m, 1H, OCH$_2$CH$_2$CH$_2$'); 2.32 (s, 3H, SAc); 1.97-1.99 (m, 6H, 2×Ac); 1.85-1.92 (m, 5H, NHAc, OCH$_2$CH$_2$, OCH$_2$CH$_2$') ppm. $^{13}$C NMR (150 MHz, CDCl$_3$, 300K): δ 195.8; 170.5; 170.3; 169.7; 166.5; 165.9; 165.7; 165.1; 164.6; 133.9; 133.5; 133.2; 133.1; 133.1; 133.0; 132.8; 129.3-130.0; 128.6-129.2; 128.0-128.4; 101.3 (βGalC-1); 97.4 (αGlcNAcC-1); 92.9 (αGa1C-1); 76.1; 73.2; 71.8; 71.4; 70.8; 69.1; 67.9; 67.8; 67.3; 66.8; 66.0; 64.6; 62.5; 61.8; 61.1; 51.9; 30.7; 29.8; 29.3; 25.5; 23.2; 20.8; 20.5 ppm. ESI-TOF HRMS [C$_{78}$H$_{75}$NO$_{26}$S+H]$^+$ calc. m/z=1474.4376, found 1474.4222.

Allyl 2,3,4,6-tetra-O-acetyl-β-D-galactopyranosyl-(1→4)-2-deoxy-2-acetamido-3,6-di-O-benzoyl-α-D-glucopyranoside (19). To a solution of acceptor 13 (Danac et al. 2007) (3.60 g, 7.63 mmol) and donor 18 (Schmidt and Michel 1980) (14.0 g, 28.42 mmol) in 60 mL anhydrous CH$_2$Cl$_2$, BF$_3$-OEt$_2$ (1.93 mL, 15.25 mmol) was added and immediately brought to 35-40° C. After 3 h, Et$_3$N (2.35 mL, 16.87 mmol) was added. The solution was washed one time with a saturated NaHCO$_3$ solution, and the aqueous layer was extracted with CH$_2$Cl$_2$. The organic phases were combined, dried over MgSO$_4$, filtered, concentrated, and purified by column chromatography on silica gel (EtOAc/Hex 2.3:1) to give 19 as a white powder (5.10 g, 83%). [α]$^{22}_D$ 56.6 (c=1 in CHCl$_3$); R$_f$=0.30 (EtOAc/hexanes 2:1); $^1$H NMR (600 MHz, CDCl$_3$, 300K) δ 8.07; 7.61; 7.52; 7.47 (4 m, 10H, 2×Bz); 5.91 (m, 1H, OCH$_2$CHCH$_2$); 5.85 (d, 1H, $^3J_{H1/H2}$=9.6 Hz, NH); 5.62 (dd, 1H, $^3J_{H2/H3}$=11.0 Hz, $^3J_{H3/H4}$=8.3 Hz, αGlcNAcH-3); 5.30 (m, 1H, OCH$_2$CHCH$_2$); 5.25 (m, 1H, OCH$_2$'CHCH$_2$); 5.13 (m, 1H, βGalH-4); 5.10 (dd, 1H, $^3J_{H2/H3}$=10.3 Hz, βGalH-2); 4.91 (d, 1H, $^3J_{H1/H2}$=3.4 Hz, αGlcNAcH-1); 4.82 (dd, 1H, $^3J_{H3/H4}$=3.4 Hz, βGalH-3); 4.69 (m, 1H, αGlcNAcH-2); 4.61 (d, 1H, $^3J_{H1/H2}$=8.3 Hz, βGalH-1); 4.47 (m, 1H, αGlcNAcH-2); 4.41 (dd, 1H, $^2J_{H6/H6'}$=4.1 Hz, $^3J_{H5/H6}$=11.7 Hz, αGlcNAcH-6'); 4.22 (m, 1H, OCH$_2$CHCH$_2$); 4.07-4.15 (m, 2H, αGlcNAcH-4, αGlcNAcH-5); 4.03 (m, 1H, OCH$_2$CHCH$_2$'); 3.64 (dd, 1H, $^3J_{H5/H6}$=8.3 Hz, $^2J_{H6/H6'}$=11.0 Hz, βGalH-6); 3.48 (dd, 1H, $^3J_{H5/H6}$=5.5 Hz, βGalH-6'); 3.36 (dd, 1H, 6.2 Hz, 8.3 Hz, βGalH-5); 1.80-2.10 (m, 15H, 4×Ac, NHAc) ppm. $^{13}$C NMR (150 MHz, CDCl$_3$, 300K): δ 170.2; 169.9; 169.4; 166.4; 166.1; 133.6; 133.5; 133.2; 129.8; 129.7; 128.7; 128.6; 118.6; 101.1 (βGalC-1); 96.5 (αGlcNAcC-1); 76.4; 72.2; 71.0; 70.6; 69.4; 68.9; 68.8; 66.3; 62.6; 60.0; 52.2; 23.2; 20.5-20.8 ppm. ESI-TOF HRMS [C$_{39}$H$_{45}$NO$_{17}$+H]$^+$ calc. m/z=800.2766, found 800.2864; [C$_{39}$H$_{45}$NO$_{17}$+Na]$^+$ calc. m/z=822.2585, found 822.2022; [C$_{39}$H$_{45}$NO$_{17}$+K]$^+$ calc. m/z=838.2325, found 838.1110.

3-(acetylthio)propyl 2,3,4,6-tetra-O-acetyl-β-D-galactopyranosyl-(1→4)-2-deoxy-2-acetamido-3,6-di-O-benzoyl-α-D-glucopyranoside (20). To a solution of 19 (0.050 g, 0.063 mmol) and AIBN (0.010 g, 0.063 mmol) in anhydrous THF (3 mL), thioacetic acid (0.045 mL, 0.63 mmol) was added and stirred under argon for 5 min. The solution was then placed in a Rayonet UV reactor (350 nm) stirred for 12 h under water cooling (~rt). The solution was concentrated by two co-evaporations with toluene, and purified by column chromatography on silica gel (EtOAc/Hex 2:1) to give 20 as a white powder (0.046 g, 84%). $[\alpha]^{22}_D$ 45.6 (c=0.9 in $CHCl_3$); $R_f$=0.25 (EtOAc/hexanes 2:1); $^1H$ NMR (600 MHz, $CDCl_3$, 300K) δ 8.08; 7.61; 7.52; 7.47 (4 m, 10H, 2×Bz); 6.15 (d, 1H, $^3J_{H1/H2}$=9.6 Hz, NH); 5.58 (dd, 1H, $^3J_{H2/H3}$=10.3 Hz, $^3J_{H3/H4}$=8.3 Hz, αGlcNAcH-3); 5.13 (m, 1H, βGalH-4); 5.10 (dd, 1H, $^3J_{H2/H3}$=10.3 Hz, βGalH-2); 4.80-4.84 (m, 2H, αGlcNAcH-1, βGalH-3); 4.70 (m, 1H, αGlcNAcH-6); 4.60 (d, 1H, $^3J_{H1/H2}$=8.3 Hz, βGalH-1); 4.48 (m, 1H, αGlcNAcH-2); 4.40 (dd, 1H, $^2J_{H6/H6'}$=4.1 Hz, $^3J_{H5/H6}$=11.7 Hz, αGlcNAcH-6'); 4.09 (m, 2H, αGlcNAcH-4, αGlcNAcH-5); 3.80 (m, 1H, $OCH_2CH_2CH_2$); 3.61 (dd, 1H, $^3J_{H5/H6}$=8.3 Hz, $^2J_{H6/H6'}$=11.0 Hz, βGalH-6); 3.47 (m, 2H, $OCH_2'CH_2CH_2$, βGalH-6'); 3.37 (m, 1H, βGalH-5); 3.10 (m, 1H, $OCH_2CH_2CH_2$); 2.96 (m, 1H, $OCH_2CH_2CH_2'$); 2.35 (s, 3H, SAc); 1.85-2.05 (m, 17H, NHAc, 4×Ac, $OCH_2CH_2CH_2$) ppm. $^{13}C$ NMR (150 MHz, $CDCl_3$, 300K): δ 195.7; 170.5; 170.1; 169.9; 169.4; 166.3; 166.1; 133.5; 129.8; 129.7; 128.7; 128.6; 101.1 (βGalC-1); 97.4 (αGlcNAcC-1); 76.4; 72.2; 71.0; 70.6; 69.4; 68.9; 66.3; 66.1; 62.6; 60.0; 52.1; 30.7; 29.8; 29.3; 25.6; 23.1; 20.5-20.8 ppm. ESI-TOF HRMS $[C_{41}H_{49}NO_{18}S+H]^+$ calc. m/z=876.2749, found 876.3192; $[C_{41}H_{49}NO_{18}S+Na]^+$ calc. m/z=898.2568, found 898.2413.

3-(acetylthio)propyl 2-deoxy-2-acetamido-3,4,6-tri-O-acetyl-β-D-glucopyranoside (22). To a solution of 21 (Kiso and Anderson 1979) (0.081 g, 0.209 mmol) and AIBN (0.034 g, 0.209 mmol) in anhydrous THF (5 mL), thioacetic acid (0.149 mL, 2.09 mmol) was added and stirred under argon for 5 min. The solution was then placed in a Rayonet UV reactor (350 nm) and stirred for 12 h under water cooling (~rt). The solution was concentrated by two co-evaporations with toluene, and purified by column chromatography on silica gel ($CHCl_3$/MeOH 25:1) to give 22 as a white powder (0.082 g, 85%). $[\alpha]^{26}_D$ 11.9 (c=1 in $CHCl_3$); $R_f$=0.30 (MeOH/$CHCl_3$ 1:9) $^1H$ NMR (600 MHz, $CDCl_3$, 300K) δ 6.20 (d, 1H, $^3J_{H1/H2}$=8.9 Hz, NH); 5.17 (dd, 1H, $^3J_{H2/H3}$=8.9 Hz, $^3J_{H3/H4}$=10.3 Hz, H-3); 5.02 (dd, 1H, $^3J_{H4/H5}$=9.62 Hz, H-4); 4.50 (d, 1H, $^3J_{H1/H2}$=8.3 Hz, H-1); 4.20 (dd, 1H, $^3J_{H5/H6}$=12.4 Hz, $^2J_{H6/H6'}$=4.8 Hz, H-6); 4.06 (dd, 1H, $^3J_{H5/H6}$=12.4 Hz, H-6'); 3.92 (m, 1H, H-2); 3.85 (m, 1H, $OCH_2CH_2CH_2$); 3.64 (m, 1H, H-5); 3.42 (m, 1H, $OCH_2'CH_2CH_2$); 3.00 (m, 1H, $OCH_2CH_2CH_2$); 2.75 (m, 1H, $OCH_2CH_2CH_2'$); 2.28 (s, 3H, SAc); 1.80-2.10 (m, 13H, NHAc, 3×Ac, $OCH_2CH_2CH_2$); 1.69 (m, 1H, $OCH_2CH_2'CH_2$) ppm. $^{13}C$ NMR (150 MHz, $CDCl_3$, 300K): δ 196.7; 171.0; 170.8; 170.6; 169.5; 100.8 (C-1); 72.9; 71.8; 68.7; 67.5; 62.2; 54.4; 30.7; 29.4; 25.4; 23.3; 20.6-20.9 ppm. ESI-TOF HRMS $[C_{19}H_{29}NO_{10}S+H]^+$ calc. m/z=464.1590, found 464.1340; $[C_{19}H_{29}NO_{10}S+Na]^+$ calc. m/z=486.1410, found 486.1100; $[C_{19}H_{29}NO_{10}S+K]^+$ calc. m/z=502.1149, found 502.0768.

Immunization Protocol. Groups of five female C57B1/6 α1,3GalT-KO mice (Tearle et al. 1996; Thall et al. 1996) were immunized subcutaneously with 20 μg Galα(1,3)Galβ(1,4)GlcNAcα-BSA in 200 μl PBS/dose/immunization or 20 μg BSA alone in 200 μl PBS. All animals were immunized four times at 7-day intervals and sacrificed 14 days after the last immunization. Blood was collected by cardiac puncture and serum was separated through centrifugation for analysis by CL-ELISA. All animal procedures were performed according to the vertebrate animal protocols A-201211-1 and A-201411-1, approved by the University of Texas at El Paso's Institutional Animal Care and Use Committee.

Protocol for the conjugation of thiols to BSA. For the conjugation of mercaptopropyl glycosides to maleimide-activated BSA a conjugation kit "Imject Maleimide Activated Carrier Protein Spin Kit" from Thermo Scientific, product #77667, was used, and the protocol provided by the manufacturer was followed.

Tris(2-carboxyethyl)phosphine (TCEP, 0.8 mg, 2.79 μmol) was dissolved in 250 μL of Imject Maleimide Conjugation Buffer (83 mM sodium phosphate buffer, 0.1 M EDTA, 0.9 M sodium chloride, 0.02% sodium azide, pH 7.2) and added to microcentrifuge tubes containing sugar-disulfide (2.40 μmol), and stirred. After 1 hour, 10 μL was removed to determine the initial thiol concentration. Vials of maleimide-activated BSA (2 mg, 15-25 moles of maleimide/mole of BSA) were reconstituted by adding 200 μL of ultrapure water. The remaining 240 μL of sugar-conjugation buffer solution was added to each vial. Vials were flushed with argon, sealed with parafilm, and mixed for 3 hours on a shaker. Reaction Buffer was prepared (0.1 M sodium phosphate, pH 8.0, containing 1 mM EDTA) and a solution of Ellman's Reagent [5,5'-dithiobis-(2-nitrobenzoic acid)=DTNB] (4 mg DTNB in 1 mL of Reaction Buffer). After 3 hours, 18.3 μL was removed from each conjugation solution to determine the thiol concentration after the conjugation. Each sample to be tested was diluted to 250 μL with Reaction Buffer and added to a test tube containing 50 μL of Ellman's Reagent Solution and 2.5 mL of Reaction Buffer, and mixed at room temperature for 15 minutes. With a spectrophotometer set to 412 nm, the absorbance of each sample was measured. Using the molar extinction coefficient of 2-nitro-5-thiobenzoic acid (TNB, ε=14,150 $M^{-1}$ $cm^{-1}$), the concentration of sulfhydryls in each sample and the amount of sugar loaded (average: 2.0 μmol) was determined.

Conjugates were then diluted to 1 mL and added to Amicon Ultra 3K Centrifugal Filter Devices for desalting. Filters were centrifuged for 20 minutes at 4000×g, then 1 mL of ultrapure water was added to the filter, and centrifuging was continued for 20 minutes at 4000×g. The filtrate tube was then removed, and filters were inverted and centrifuged at 1000×g for 2 minutes to collect in the concentrate tube. The collected material was lyophilized, and stock solutions of the protein were prepared. The protein concentrations were determined using a Pierce BCA (bicinchoninic acid) Protein Assay Reagent kit using a spectrophotometer at a detection wavelength of 562 nm.

CL-ELISA protocol. 12 ng of each NGP were diluted in 0.2 M carbonate-bicarbonate buffer (pH 9.6), immobilized on 96-well MaxiSorp microplates (NUNC, Thermo Fisher Scientific) and incubated overnight at 4° C. Free binding sites were blocked with 200 μl/well of 1% bovine serum albumin (BSA) in 1× phosphate buffered saline (PBS, pH 7.4). 50 μl of Chagasic and normal human sera (⅟800) or purified antibodies (1 μg/ml) were added as primary antibodies diluted in 1% BSA-PBS with 0.05% Tween 20 (Promega). 50 μl of goat anti-human IgG (H+L) biotin conjugated (Thermo Fisher Scientific) (¹/₁₀,₀₀₀) diluted in 1% BSA-PBS with 0.05% Tween 20 was added as secondary antibody. 50 μl of High Sensitivity NeutrAvidin-HRP (Thermo Fisher Scientific) (⅕,₀₀₀) diluted in 1% BSA-PBS with 0.05% Tween 20 was then added. Finally, microplate was developed by adding 50 μL of SuperSignal ELISA Pico Chemiluminescent Substrate (Thermo Fisher Scientific), diluted ⅛ in 0.2 M carbonate-bicarbonate buffer, pH 9.6 with 0.1% BSA. Relative luminescent units (RLU) were obtained using a Luminoskan luminometer (Labsystems, Thermo). All incubations between steps were carried out for

Example 2

Assessment of Immune Response in A1,3Gal T-KO Mouse Model

Figure 9:
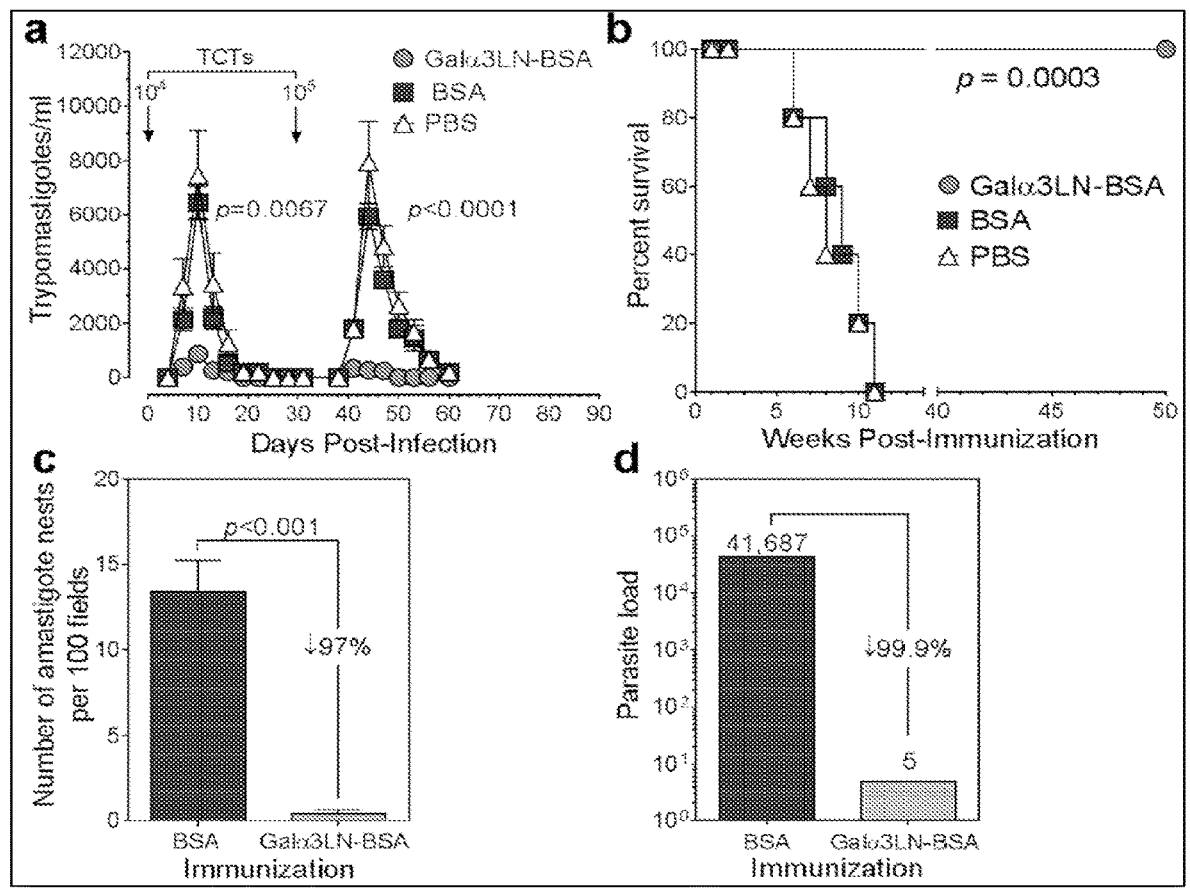
FIG. 9. Vaccination with Galα3LN-BSA fully protects α1,3GalT-KO mice against *T. cruzi* infection. Animals (n=7, per group) were vaccinated (i.p.) with four doses (at one-week intervals) of 10 µg Galα3LN-BSA, in 200 µl PBS (vehicle). The control groups (n=7, per group) were vaccinated with BSA (10 µg) or PBS alone. A week after the last immunization, Galα3LN-BSA-immunized animals showed very high titers of anti-α-Gal IgG Abs (not shown). Mice were then challenged with 10,000 mammalian-cell derived trypomastigotes (TCTs). Four weeks later, the same group was re-challenged with 10-fold higher parasite dose (100,000). Parasitemia and survival rate were followed daily. (a) Parasitemia after immunization with Galα3LN-BSA, BSA, or PBS, and two subsequent infections at days 0 and 30, respectively. (b) Survival rate. Control groups (BSA and PBS) were subjected to the same parasite challenges. (c) Number of amastigote nests in the heart of BSA-injected (control) and Galα3LN-BSA-vaccinated mice followed by parasite challenge with 10,000 TCTs. (d) qRT-PCR analysis of *T. cruzi* satellite DNA of the whole heart homogenate of BSA- and Galα3LN-BSA-vaccinated mice following parasite challenge was carried out as described. Error bars represent means+/−s.e.m. Statistics: two-tailed T-test (a and c), and log-rank (Mantel-Cox) test (b).

The immune response of α1,3GalT-KO mice (C57BL/6 background) was evaluated against the immunodominant Galα3LN epitope, covalently linked to bovine serum albumin (BSA) as carrier protein. The Galα3LN-BSA-vaccinated group showed significantly lower initial parasitemia than the control groups (BSA or PBS) (FIG. 9A). When the former group was re-challenged, the second peak of parasitemia was slightly lower than the first one. All animals (n=7) of the Galα3LN-BSA-vaccinated group survived *T. cruzi* infection (FIG. 9B). Control groups, by contrast, died within 10-12 weeks post-infection. Galα3LN-BSA-vaccinated and control animals were euthanized and the hearts were removed for histological analysis and qRT-PCR. The vaccine efficacy was supported by the very low number of parasite nests in the heart (FIG. 9C). Control groups, conversely, showed a much higher number of amastigote nests. The vaccine efficiency was further evidenced by qRT-PCR, where Galα3LN-BSA-vaccinated animals showed 8,300-fold (99.9%) lower parasite load than the BSA control (FIG. 9D). Taken together, the data clearly demonstrated that vaccination with Galα3LN-BSA is highly effective against lethal *T. cruzi* challenges in a mouse model that mimics the human humoral response against the parasite. One open question, however, is whether this glycoconjugate vaccine could elicit a helper T cell-dependent B cell-mediated protection. This would likely provide a stronger, long-term protection, as seen for glycoconjugate vaccines against bacteria.

Figure 10:
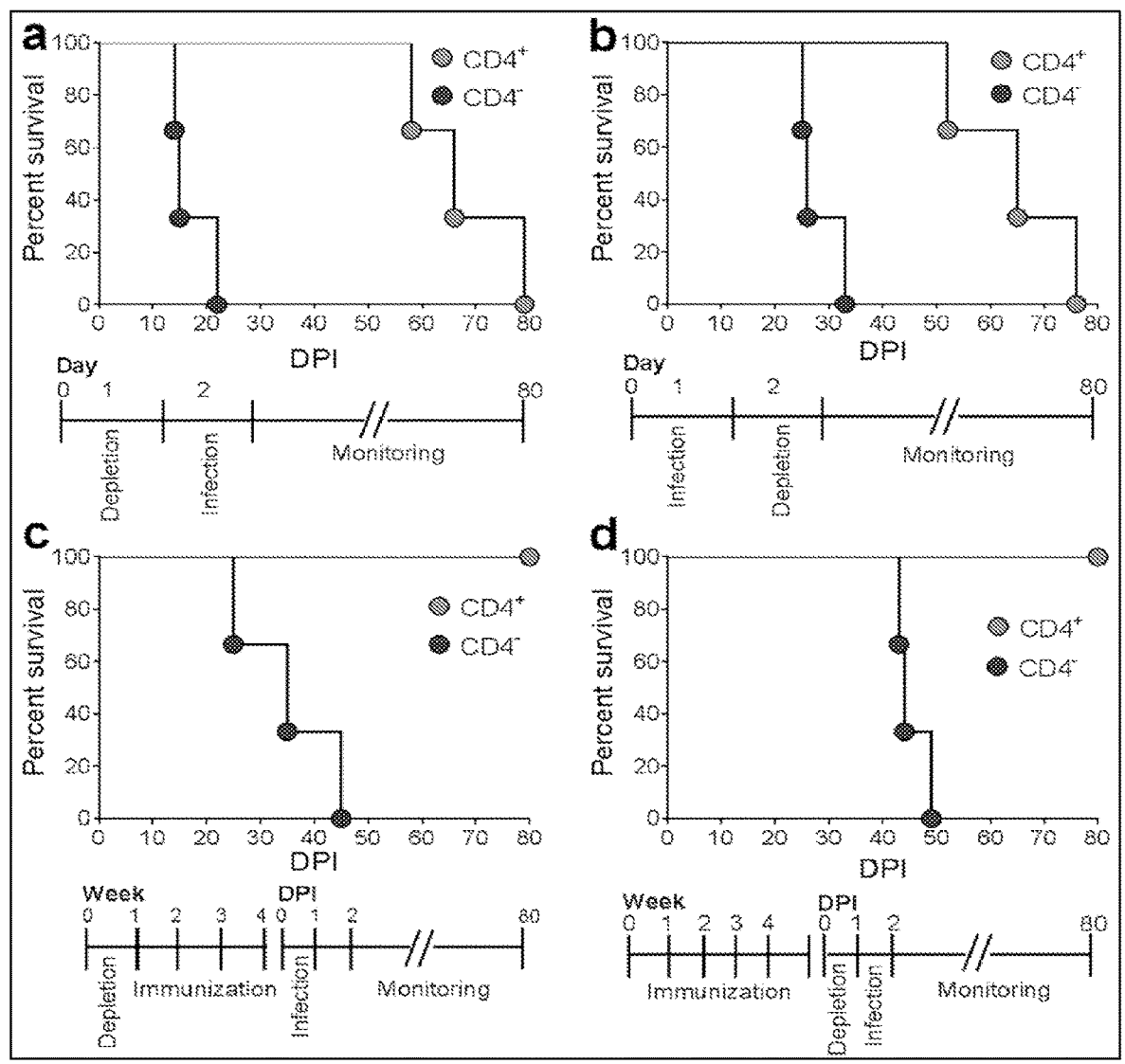
FIG. 10. CD4+ T cells are vital for the protection of α1,3GalT-KO mice by Galα3LN-BSA. (a) α1,3GalT-KO animals were depleted of CD4+ T cells and infected; (b) mice were infected and then depleted; (c) mice were depleted, immunized with Galα3LN-BSA, and then infected; and (d) mice were immunized with Galα3LN-BSA, depleted and then infected. In all groups, n=3. All infections were done with 100,000 TCTs. Data are representative of three to five independent experiments with three mice per group. DPI, days post-infection.

It is established that CD4+ T cells play a critical role in the control of ChD. Here, a protocol was developed to evaluate the role of CD4+ T cells in α1,3GalT-KO mice immunized with Galα3LN-BSA and challenged with mammalian cell tissue culture-derived *Trypanosoma cruzi* trypomastigotes (TCTs). Mice were depleted of CD4$^+$ T cells by a single injection of 500 µg anti-CD4 mAb (clone gK1.5, BD). A day later, the depletion efficiency (~98%) was assessed in the total blood by flow cytometry. Two control groups without any immunization, in which mice were depleted then infected or infected then depleted, were also evaluated. All mice infected before or after the depletion died within ~30 days, thus validating the crucial role of CD4$^+$ T cells in the α1,3GalT-KO mouse model of ChD (FIGS. 10A and 10B). To assess whether the protection of α1,3GalT-KO mice by Galα3LN-BSA-vaccination was dependent on CD4$^+$ T cells, animals were depleted before and after immunization, and then challenged with 100,000 TCTs (FIGS. 10C and 10D). In both experiments, a clear dependence on CD4$^+$ T cells for survival was seen. However, it was also evident that vaccination with Galα3LN-BSA, before or after CD4$^+$ T cell depletion, increased the survival rate when compared with non-vaccinated controls (FIGS. 10A and 10B). CD4+ T cells seem to be involved in (a) controlling *T. cruzi* infection in α1,3GalT-KO mice; and (b) effective protection by Galα3LN-BSA vaccination.

Abbreviations use throughout this specification include: α1,3-GalT-KO, α1,3-galactosyltransferase-knockout; Abs, antibodies; AcSH, thioacetic acid; AIBN, azobisisobutyronitrile; BF$_3$-Et$_2$O, boron trifluoride etherate; BSA, bovine serum albumin; Ch anti-α-Gal, anti-α-Gal antibodies purified from sera of patients with chronic Chagas disease; ChD, Chagas disease; CL-ELISA, chemiluminescent ELISA; ChHSP, pooled sera of chronic Chagas disease patients; DBU, 1,8-diazabicycloundec-7-ene; DDQ, 2,3-dichloro-5,6-dicyano-1,4-benzoquinone; DTBS, di-tertbutylsilyl; DTBS(OTf)$_2$, di-tertbutylsilyl bis(trifluoromethanesulfonate); FPLC, fast protein liquid chromatography; HF-pyr, hydrogen fluoride in pyridine; MALDI-TOF, Matrix-assisted laser desorption ionization Time-of-Flight; NGP, neoglycoprotein; NHSP, normal human serum pool; NHS anti-α-Gal, anti-α-Gal antibodies from sera of healthy individuals; NMR, nuclear magnetic resonance; PBS, phosphate-buffered saline; PMB, para-methoxybenzyl; RLU, relative luminescence units; TCEP, tris(2-carboxyethyl)phosphine; tGPI-mucins, trypomastigote-derived GPI-mucins; TMSOTf, trimethylsilyl trifluoromethanesulfonate

REFERENCES

Acosta-Serrano et al., 2007. Comparison and evolution of the surface architecture of trypanosomatid parasites In African Trypanosomes: After the Genome. In: Barry J D M R, Mottram J C & Acosta-Serrano A editor. Norwich, UK: Horizon Scientific Press. p. 319-337.

Almeida et al., 1997. *Transfusion*, 37:850-857.

Almeida et al., 1994. *The Biochemical journal*, 304 (Pt 3):793-802.

Almeida et al., 1993. *Journal of clinical laboratory analysis*, 7:307-316.

Almeida et al., 1991. *Journal of immunology*, 146:2394-2400.

Ashmus et al. 2013. *Organic & biomolecular chemistry*, 11:5579-5583.

Atassi et al., 1982. *Mol Immunol*, 19:313-321.

Avila et al., 1989. *Journal of immunology*, 142:2828-2834.

Brinkmann et al., 2001. *Bioorganic & Medicinal Chemistry Letters*, 11:2503-2506.

Buscaglia et al., 2004. *The Journal of biological chemistry*, 279:15860-15869.

Crich and Dudkin, 2001. *Journal of the American Chemical Society*, 123: 6819-6825.

Dahmén et al., 2002. *Journal of Carbohydrate Chemistry*, 21:1-12.

Danac et al., 2007. *Chem Bio Chem*, 8:1241-1245.

Ettinger et al., 1990. *Science* 249:423-425.

Fang et al., 1998. *Journal of the American Chemical Society*, 120:6635-6638.

Frasch 2000. *Parasitology today*, 16:282-286.

Galili et al., 1999. *Sub-cellular biochemistry*, 32:79-106.

Gavard et al., 2003. *European Journal of Organic Chemistry*, 2003:3603-3620.

Gazzinelli et al., 1991. *Parasite immunology*, 13:345-356.

Hanessian et al., 2001. *Tetrahedron*, 57:3267-3280.

Hendel et al., 2009. *The Journal of Organic Chemistry*, 74:8321-8331.

Houseman et al., 2003. *Langmuir*, 19:1522-1531.

Imamura et al., 2006. *Chemistry—A European Journal*, 12:8862-8870.

Izquierdo et al., 2013. *Memórias do Instituto Oswaldo Cruz*, 108:928-931.

Khamsi et al., 2012. *Carbohydrate Research*, 357:147-150.

Kiso and Anderson, 1979. *Carbohydrate Research*, 72:C12-C14.

Litjens et al., 2005. *Journal of Carbohydrate Chemistry*, 24:755-769.

Macher and Galili, 2008. *Biochimica et biophysica acta*, 1780:75-88.
Makela and Seppala, 1986. Haptens and Carriers. In: Weir D M editor. Handbook of Experimental Immunology in four Volumes. Oxford, U.K.: Blackwell Scientific Publications.
Milani and Travassos, 1988. *Brazilian journal of medical and biological research=Revista brasileira de pesquisas medicas e biologicas/Sociedade Brasileira de Biofisica* 21:1275-1286.
Plaza-Alexander and Lowary, 2013. *Arkivoc*, ii:112-122.
Qian et al., 1999. *Journal of the American Chemical Society*, 121:12063-12072.
Schmidt and Michel, 1980. *Angew Chem Int Edit*, 19:731-732.
Sherman et al., 2001. *Carbohydrate Research*, 336:13-46.
Soares et al., 2012. *The American journal of tropical medicine and hygiene*, 87:87-96.
Stevenson and Furneaux, 1996. *Carbohydrate Research*, 284:279-283.
Tearle et al., 1996. *Transplantation*, 61:13-19.
Thall et al., 1996. *Transplantation proceedings*, 28:556-557.
Travassos and Almeida, 1993. *Springer Semin Immunopathol*, 15:183-204.
Vic et al., 1997. *Chemical Communications:*169-170.
Wang et al., 2005. *Tetrahedron*, 61:4313-4321.
Wilkinson, 1996. *Progress in lipid research*, 35:283-343.
Yoshida et al., 2001. *Carbohydrate Research*, 335:167-180.

The invention claimed is:

1. A neoglycoconjugate comprising a trisaccharide coupled to a carrier, wherein the trisaccharide is Galα(1,3)Galβ(1,4)Glcα, Galα(1,2)Galβ(1,4)GlcNAcα, Galα(1,2)Galβ(1,4)Glcα, or Galα(1,2)Galβ(1,4)Glcβ.

2. The neoglycoconjugate of claim 1, further comprising a linker connecting the trisaccharide to the carrier.

3. The neoglycoconjugate of claim 1 wherein the carrier is a protein carrier.

4. The neoglycoconjugate of claim 3, wherein the protein carrier is bovine serum albumin.

5. The neoglycoconjugate of claim 1, wherein the carrier is peptide.

6. The neoglycoconjugate of claim 5, wherein the peptide is a T cell epitope.

7. The neoglycoconjugate of claim 1, wherein the trisaccharide comprises a terminal galactose residue.

8. A method of detecting a parasite comprising:
   (a) contacting a blood sample from a subject with the neoglycoconjugate of claim 1, wherein the neoglycoconjugate forms a complex with antibodies in the blood sample that bind a glycan having a terminal αGal; and
   (b) detecting the formation of an antibody-neoglycoconjugate complex.

9. The method of claim 8, wherein the subject is suspected of having Chagas disease, cutaneous and visceral leishmaniasis, or malaria.

10. A method for inducing an immune response against *T. cruzi* in a human comprising administering the neoglycoconjugate of claim 1, wherein an immune response is generated against a *T. cruzi*.

11. The method of claim 10, wherein the carrier is bovine serum albumin.

* * * * *